US011185114B2

(12) United States Patent
Muhlenfeld

(10) Patent No.: US 11,185,114 B2
(45) Date of Patent: *Nov. 30, 2021

(54) ADJUSTABLE SUPPORT GARMENT WITH HARNESS SYSTEM

(71) Applicant: NIKE, Inc., Beaverton, OR (US)

(72) Inventor: Stephanie Muhlenfeld, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 301 days.

This patent is subject to a terminal disclaimer.

(21) Appl. No.: 16/454,312

(22) Filed: Jun. 27, 2019

(65) Prior Publication Data

US 2019/0313705 A1    Oct. 17, 2019

Related U.S. Application Data

(63) Continuation of application No. 15/458,174, filed on Mar. 14, 2017, now Pat. No. 10,383,373.
(Continued)

(51) Int. Cl.
*A41C 3/00* (2006.01)
*A41C 3/02* (2006.01)
(Continued)

(52) U.S. Cl.
CPC .............. *A41C 3/0028* (2013.01); *A41B 1/08* (2013.01); *A41C 3/005* (2013.01); *A41C 3/02* (2013.01);
(Continued)

(58) Field of Classification Search
CPC ..... A41C 3/0028; A41C 3/0057; A41C 3/005; A41C 3/02; A41C 3/08; A41C 3/12;
(Continued)

(56) References Cited

U.S. PATENT DOCUMENTS 2,341,032 A    2/1944 Freed et al.
2,423,550 A    7/1947 McMahon
(Continued)

FOREIGN PATENT DOCUMENTS

CN    201238619 Y    5/2009
CN    203735495 U    7/2014
(Continued)

OTHER PUBLICATIONS

Extended European Search Report received for European Patent Application No. 20164947.2, dated Jul. 24, 2020, 8 pages.
(Continued)

*Primary Examiner* — Gloria M Hale
(74) *Attorney, Agent, or Firm* — Shook, Hardy & Bacon L.L.P.

(57) ABSTRACT

A harness system for adjusting support of a garment is provided herein. The garment with a harness system includes a body and a liner having harness straps. The harness straps slide through openings in shoulder straps of the body. The harness straps are then laced through a series of maintainers in the back of the body. The harness straps having terminally-located tabs that may be pulled from the back of the body toward the front of the body and affixed thereto. The placement of the tabs, when pulled toward the front of the body and attached thereto, determines the fit and support of the garment. By manipulating the tabs of the harness system, a wearer may adjust the length of the harness straps, back and posture support, and the lift provided by the liner. The harness system creates a customizable fit and support level.

20 Claims, 16 Drawing Sheets

Related U.S. Application Data

(60) Provisional application No. 62/314,118, filed on Mar. 28, 2016.

(51) Int. Cl.

| | | |
|---|---|---|
| *A41B 1/08* | (2006.01) | |
| *A41C 3/08* | (2006.01) | |
| *A41C 3/12* | (2006.01) | |
| *A41D 7/00* | (2006.01) | |
| *A41D 15/00* | (2006.01) | |
| *A41D 27/00* | (2006.01) | |
| *A61F 5/02* | (2006.01) | |

(52) U.S. Cl.
CPC .............. *A41C 3/08* (2013.01); *A41C 3/12* (2013.01); *A41D 7/00* (2013.01); *A41D 15/00* (2013.01); *A41D 27/00* (2013.01); *A61F 5/02* (2013.01); *A41C 3/0057* (2013.01)

(58) Field of Classification Search
CPC . A41B 1/08; A41D 7/00; A41D 15/00; A41D 27/00; A61F 5/02
USPC ............... 2/44, 96, 105, 106; 450/30–33
See application file for complete search history.

(56) References Cited

U.S. PATENT DOCUMENTS

| | | | |
|---|---|---|---|
| 2,581,036 A | 1/1952 | McIlhinney | |
| 3,071,140 A | 1/1963 | Adler | |
| 3,212,503 A | 10/1965 | Gorman | |
| 4,276,884 A | 7/1981 | O'Daniels | |
| 4,300,568 A | 11/1981 | Blanckmeister | |
| 6,023,785 A | 2/2000 | Johnson | |
| 6,282,717 B1 | 9/2001 | Ng | |
| D475,835 S | 6/2003 | Hoffman et al. | |
| 7,452,260 B2 | 11/2008 | Redenius | |
| 7,628,675 B2 | 12/2009 | Staub | |
| 8,047,893 B2 | 11/2011 | Fenske | |
| 8,172,639 B2 | 5/2012 | Swendseid | |
| 8,500,513 B2 | 8/2013 | Campbell | |
| 10,383,373 B2 * | 8/2019 | Muhlenfeld | A41B 1/08 |
| 2011/0081827 A1 | 4/2011 | Williams | |
| 2011/0191944 A1 | 8/2011 | Lescom et al. | |
| 2011/0197330 A1 | 8/2011 | Simpson | |
| 2012/0090078 A1 | 4/2012 | von Olnhausen | |
| 2013/0012853 A1 | 1/2013 | Brown | |
| 2013/0326788 A1 | 12/2013 | Bell | |
| 2014/0256222 A1 | 9/2014 | Silver et al. | |
| 2014/0349550 A1 | 11/2014 | Campbell | |
| 2015/0079876 A1 | 3/2015 | Betts | |
| 2016/0206467 A1 | 7/2016 | Glace et al. | |
| 2017/0273365 A1 * | 9/2017 | Muhlenfeld | A41C 3/12 |
| 2018/0325185 A1 | 11/2018 | Sakai | |
| 2019/0313705 A1 * | 10/2019 | Muhlenfeld | A41D 7/00 |

FOREIGN PATENT DOCUMENTS

| | | |
|---|---|---|
| EP | 1696753 B1 | 7/2008 |
| GB | 1122811 A | 8/1968 |
| NL | 2001215 C2 | 2/2009 |
| WO | 2014144294 A2 | 12/2010 |

OTHER PUBLICATIONS

Intention to Grant received for European Patent Application No. 17717034.7, dated May 11, 2020, 7 pages.
Communication under Rule 71(3) dated Oct. 2, 2019 in European Patent Application No. 17717034.7, 57 pages.
Office Action received for European Patent Application No. 20164947.2, dated Apr. 9, 2021, 4 pages.

* cited by examiner

ADJUSTABLE SUPPORT GARMENT WITH HARNESS SYSTEM

CROSS-REFERENCE TO RELATED APPLICATIONS

This patent application, entitled "Adjustable Support Garment with Harness System", is a application of U.S. Pat. No. 10,383,373, filed on 14 Mar. 2017 and entitled "Adjustable Support Garment With Harness System," which claims the benefit of and priority to U.S. Provisional Application No. 62/314,118, filed on 28 Mar. 2016, entitled "Adjustable Support Garment With Harness System," which are all herein incorporated by reference in their entireties.

STATEMENT REGARDING FEDERALLY SPONSORED RESEARCH OR DEVELOPMENT

Not applicable.

TECHNICAL FIELD

The present invention relates to a garment having adjustable support provided by harness features.

BACKGROUND

Conventional support garments, such as bras, often lack features that enable a wearer to customize the amount of support provided by the bra. Further, when features such as hook closures or strap adjustment features are provided, they are often difficult for the wearer to access or may not be intuitive to use.

BRIEF DESCRIPTION OF THE DRAWINGS

The present aspects are described in detail below with reference to the attached drawing figures, wherein.

DETAILED DESCRIPTION

Figure 1:
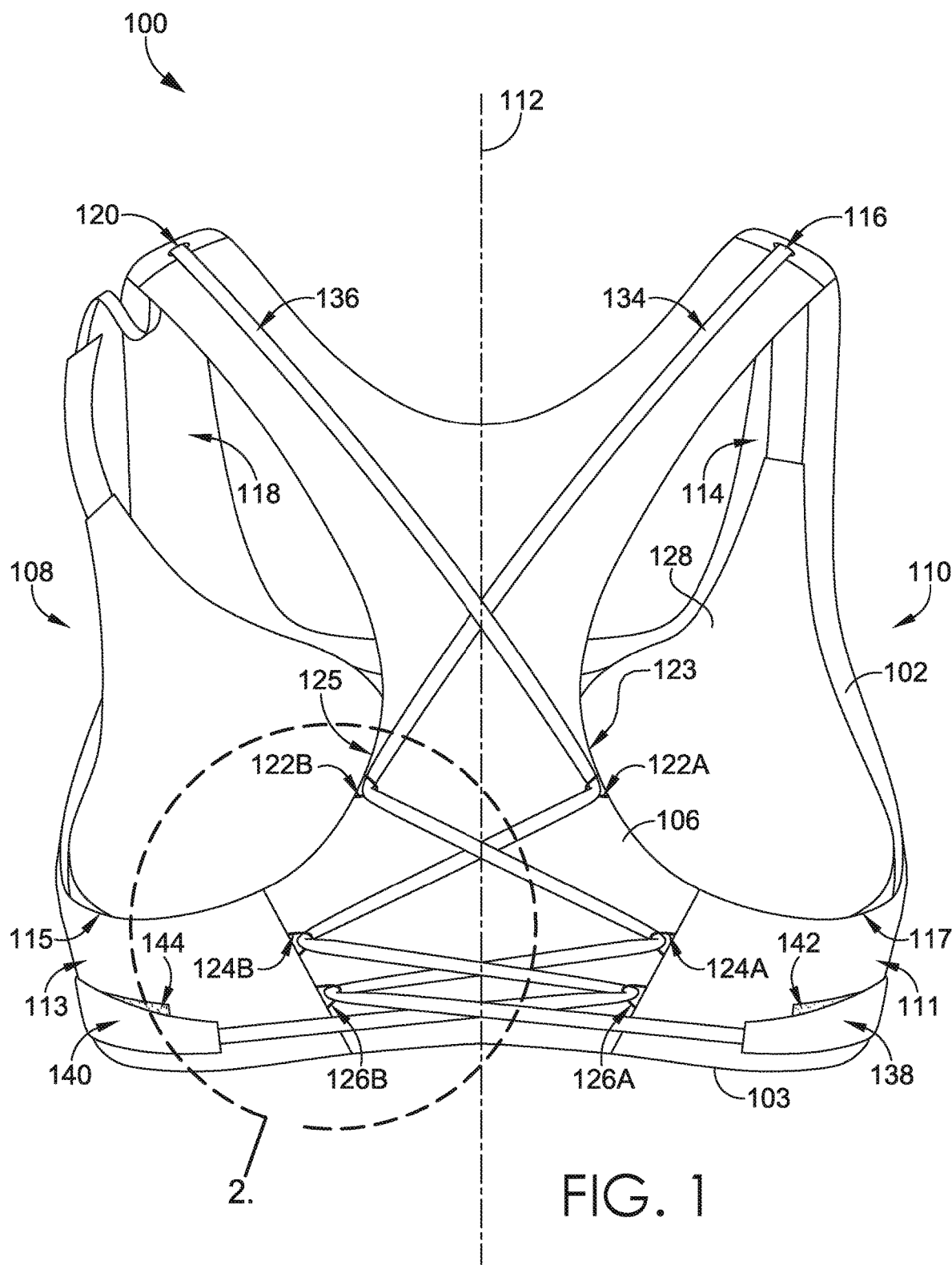
FIG. 1 depicts a rear view of a bra having adjustable support provided by a harness system, in accordance with an aspect herein.

Present aspects described herein are intended in all respects to be illustrative rather than restrictive. Alternative aspects will become apparent to those of ordinary skill in the art to which the present aspects pertain without departing from its scope. From the following, it will be seen that aspects herein are well adapted to attain all the ends and objects set forth above, together with other advantages that are obvious and inherent. It will be understood that certain features and subcombinations are of utility and may be employed without reference to other features and subcombinations. This is contemplated by and is within the scope of the claims.

An adjustable support harness system utilized in a garment, such as a bra, is provided herein. The adjustable support harness system, as utilized in a bra, for example, includes a pair of harness straps, which are coupled to a liner or a cup liner at one end and to a tab structure (e.g., a tab) at the opposite end. Each of the harness straps are configured to be fed through an aperture or opening in a corresponding right or left strap of the body of the garment. These openings are sized to allow the harness straps to slide through said openings and maintain the placement and orientation of the harness straps during adjustment, in some aspects. The harness straps are then laced through a series of maintainers or fittings that are integrated with or coupled to the exterior of a back portion of the garment. A maintainer may be an integrally formed structure or fitting of the bra body or may be an external structure or fitting that is coupled to the bra body, in aspects. Exemplary maintainers may include a loop, ring, a d-ring, a hook, a lace hook, a slide, a grommet, an eyelet, an adjuster slide, an aperture, an opening, and/or a clasp. Exemplary maintainers may include materials that exhibit a degree of rigidity so as to maintain an eye, an opening, or a loop-like shape in a resting state. The configuration of the series of maintainers may help to reduce collapse of the bra body shoulder straps during adjustment.

In order to adjust the garment using the adjustable support harness system, the tabs may be pulled or manipulated to tighten or loosen each of the harness straps, which in turn adjusts the liner at the other end of the harness straps. The tabs are generally pulled from the back of the body, wrapped around the sides of the body, and are affixed at or near the front and/or sides of the body. However, it will be understood by those having skill in the art that the tabs may be accessible at or near the front and/or sides of the bra body for convenience in adjustment.

Because of the interconnection between the liner, harness straps, openings in the shoulder straps, and maintainers, a wearer can adjust the fit of the harness straps, a level of back or posture support, and/or the degree of lift of the liner with a single manipulation of the tab of the adjustable support harness system. Additionally, the harness system may be configured to provide a same-side adjustment. For example, the right harness strap and a first section of the liner are adjusted by manipulating a right tab, while the fit and support of the left harness strap and a second section of the liner is similarly adjusted by manipulating a left tab. The same-side adjustment feature reduces confusion for a wearer and improves the ease in which the harness system may be adjusted. Alternatively, the harness system may be configured to provide an opposite-side adjustment. For example, the right harness strap and the first section of the liner may be adjusted by manipulating a left tab, while the fit and support of the left harness strap and the second section of the liner may be adjusted by manipulating a right tab. Although a same-side adjustment feature is provided in the exemplary figures of this disclosure, these figures should not be construed as limiting the disclosure to a same-side adjustment feature, as an opposite-side adjustment feature may be used and is considered to be within the scope of this disclosure.

For simplicity, a bra or bra-type garment is described herein. However, the discussion of the adjustable harness system as useable with a bra should not be construed as limiting, and other clothing or garments are considered to be within the scope of the disclosure. Exemplary garments that use the adjustable harness system described herein may include a camisole, a shirt, a tank top, a blouse, a bralette, a dress, and swimwear, for example. Accordingly, it will be understood that the adjustable harness system may be used with relation to other garments and the examples provided by the figures herein are merely illustrative in nature.

Additionally, it will be understood that, generally, directional descriptions used herein, such as left or right, front or back, up or down, are used relative to basic anatomical convention in order to provide consistency and alleviate confusion in the description of the adjustable support harness system when shown from the various vantage points provided in the figures herein. As an example, directional descriptions are used with respect to the garment being in an as-worn configuration with the wearer standing in the anatomical position.

Accordingly, in one aspect, an article of apparel is provided. The article comprises a body. The body comprises at least a front portion and a back portion, each having a lower margin, in one aspect. The body also comprises a first side with respect to a hypothetical midline axis that bisects the body into generally equal right and left halves, in some aspects. And the body further comprises a second side with respect to the hypothetical midline axis, in one aspect. The body comprises a first shoulder strap having a first aperture and a second shoulder strap having a second aperture, in aspects. The back portion of the body comprises at least a first pair of maintainers, in some aspects, such that each maintainer is positioned opposite the other maintainer with respect to the hypothetical midline axis. In further aspects, the back portion comprises a second pair of maintainers. In one further aspect, each of the maintainers of the first pair of maintainers is attached to the back portion at a first distance from the hypothetical midline axis, and each maintainer of the second pair of maintainers is attached to the back portion at a second distance from the hypothetical midline axis, wherein the second distance is greater than the first distance. And in some further aspects, the back portion further comprises a third pair of maintainers, wherein a first lengthwise distance, as measured along the hypothetical midline axis, between the first pair of maintainers and the second pair of maintainers is greater than a second lengthwise distance between the third pair of maintainers and the second pair of maintainers.

Continuing, the article further comprises a liner, in aspects. The liner is positioned adjacent and internal to the body, in aspects. In some aspects, at least a portion of the liner is coupled to the front portion of the body. The liner has a first harness strap and a second harness strap, in some aspects. In one aspect, the first and second harness straps are positioned adjacent to the first and second shoulder straps. In some aspects, the first harness strap is adapted to pass through the first aperture and at least one maintainer of the first pair of maintainers. In one aspect, the first harness strap has a terminally located first tab. In some aspects, the second harness strap is adapted to pass through the second aperture and at least one maintainer of the first pair of maintainers, and further has a terminally located second tab. In aspects, the first side of the body includes a first attachment element to which the first tab is adapted to be attached and the second side includes a second attachment element to which the second tab is adapted to be attached. In further aspects, the first attachment element and the second attachment element are located proximate to the lower margin. The first attachment element and the second attachment element, in some aspects, include one or more fasteners useable for removeably attaching to the first tab and the second tab, respectively. In one aspect, the liner further comprises a first support pad and a second support pad, the first support pad and second support pad extending inwardly from a surface plane of the liner. In one further aspect, the first and second support pads are embedded between two or more layers of material of the liner.

Another aspect provides for a garment having adjustable support provided by a harness system. The garment comprises a body. In one aspect, the body comprises, at least, a front portion, a first side with respect to a hypothetical vertical midline axis, and a second side with respect to the hypothetical vertical midline axis. The body also comprises, in one aspect, a first shoulder strap having a first aperture and a second shoulder strap having a second aperture. The body comprises a back portion, in aspects. The back portion of the body comprises, at least, a first set of maintainers and a second set of maintainers. In some aspects, each set of maintainers having, at least, a first side maintainer and a second side maintainer. In such aspects, the first side maintainer may be attached to the back portion opposite a second side maintainer also attached to the back portion with respect to the hypothetical vertical midline axis. And, in some aspects, the first set of maintainers is attached to the back portion above the second set of maintainers, with respect to a lower margin of the body. In one further aspect, the first set of maintainers is attached to the back portion at a first lengthwise distance from the lower margin as measured along the hypothetical vertical midline axis, and wherein the first lengthwise distance facilitates distribution of tensional forces during adjustment. In one aspect, each maintainer of the second pair of maintainers is positioned at one or more seam lines. The garment further comprises a liner. In one aspect, the liner is attached to an interior surface of the body at one or more locations. In some aspects, the liner has a first section and a second section. The first section of the liner comprises a first harness strap and the second section of the liner comprises a second harness strap, in some aspects. In a further aspect, the first section and the second section of the liner are attached to the interior of the front portion of the body at one or more locations. In one aspect, the first harness strap is adapted to pass through the first aperture, cross the hypothetical vertical midline axis, and sequentially pass through at least one maintainer of the first set of maintainers and at least one maintainer of the second set of maintainers. In a further aspect, the first harness strap terminates in a right tab. In one aspect, the second harness strap is adapted to pass through the second aperture, cross the hypothetical vertical midline axis, and sequentially pass through at least one maintainer of the first set of maintainers and at least one maintainer of the second set of maintainers. In a further aspect, the second harness strap terminates in a second tab. The first side of the body includes a first attachment element to which the first tab is adapted to be attached, and the second side of the body includes a second attachment element to which the second tab is adapted to be attached, in aspects. The attachment of the first tab to the first attachment element shifts the first section of the liner from a first support position to a second support position, and the attachment of the second tab to the second attachment element shifts the second section of the liner from a first support position to a second support position, in aspects. And in one aspect, each of the first and second sections of the liner include at least a first zone and a second zone, the first zone having a first molding characteristic and the second zone having a second molding characteristic different than the first molding characteristic. In such an aspect, the first molding characteristic has a reduced modulus of elasticity relative to the second molding characteristic, for example. Additionally or alternatively, in one aspect, the first zone and the second zone are formed from the same one or more materials. In one aspect, the first zone is located superior to the second zone with respect to the lower margin.

In yet another aspect, an article of apparel having adjustable support provided by a harness system is provided. The article comprises a body. The body comprises, at least, a front portion, a first side with respect to a hypothetical vertical midline axis, and a second side with respect to the hypothetical vertical midline axis, in aspects. The body further comprises a first shoulder strap coupled to the front portion, the first shoulder strap having a first aperture adjacent to where the first shoulder strap is coupled to the front portion, in one aspect. And, in one aspect, the body comprises a second shoulder strap coupled to the front portion, the second shoulder strap having a second aperture adjacent to where the second shoulder strap is coupled to the front portion. In aspects, the body comprises a back portion, and the back portion comprises at least a first pair of maintainers, a second pair of maintainers, and a third pair of maintainers. In one aspect, each pair of maintainers has a first maintainer placed opposite a second maintainer with respect to the hypothetical vertical midline axis. In some aspects, with respect to a lower margin of the body, the first pair of maintainers is positioned superior to the second pair of maintainers and the second pair of maintainers is positioned superior to the third pair of maintainers. The article further comprises a liner having a first section and a second section. In one aspect, each of the first and second sections comprise at least a first zone and a second zone, the first zone having greater elasticity than the second zone. The first section of the liner further comprises, in one aspect, a first harness strap extending from the first zone of the first section. And the first harness strap is adapted to pass through the first aperture and sequentially pass through at least one maintainer of the first, second, and third pairs of maintainers, wherein the first harness strap passes between the first side and the second side an even number of times, in some aspects. The first harness strap terminates at a first tab, in one aspect. The second section of the liner further comprises a second harness strap extending from the first zone of the second section, in aspects. In one aspect, the second harness strap is adapted to pass through the second aperture and sequentially pass through at least one maintainer of the first, second, and third pairs of maintainers, wherein the second harness strap passes between the first side and the second side an even number of times. In some aspects, the second harness strap terminates at a second tab. In some aspects, the first side of the body further comprises a first attachment element to which the first tab is adapted to be attached. And in some aspects, the second side of the body further comprises a second attachment element to which the second tab is adapted to be attached. Attachment of the first tab to the first attachment element shifts the first section of the liner from a first support position to a second support position, and attachment of the second tab to the second attachment element shifts the second section of the liner from a first support position to a second support position, in aspects.

With reference now to FIG. 1, a rear view of a support garment such as a bra having an adjustable support harness system is provided in accordance with an aspect herein. As illustrated in FIG. 1, the bra 100 comprises a bra body 102 that acts as an exterior barrier, outer layer, and/or shell structure of the bra 100. In some aspects, the bra body 102 provides a support structure for stabilizing the harness system components during adjustment of the bra 100. As will be understood, the term "bra body" should not be construed as limiting, as a body of any garment type is capable of having the adjustable support harness system as described herein and is considered to be within the scope of this disclosure. A body might refer to one or more fabric panels of a camisole, a shirt, a tank top, or a dress, for example. In one exemplary aspect, the bra body 102 may include one or more panels of fabric and/or material. In another exemplary aspect, the bra body 102 may be constructed using a continuous panel of fabric to provide a seamless or nearly seamless garment.

In one aspect, the bra body 102 comprises one or more panels of a fabric having at least one of a compression characteristic, a moisture wicking capability, and/or a coating that increases the rigidity of the bra body fabric. As used herein, exemplary compression characteristics may include a modulus of elasticity (e.g., a measurement of a material or substance's resistance to elastic non-permanent deformation), wherein as the modulus increases, the amount of elasticity provided by a material decreases. Materials having an increased or high modulus of elasticity may provide for a "lockdown" characteristic that reduces or minimizes elasticity and increases support of the structure. Exemplary materials having a high or increased modulus of elasticity include polyester, cotton duck, twill, and linen. Exemplary materials having a low modulus of elasticity include elastane and some jersey fabrics. One or more of the materials may be coated or treated with polyurethane (PU), thermoplastic polyurethane (TPU), silicone, and the like, for example, in order to increase the modulus of elasticity of one or more portions of a garment. It will be understood that compression capabilities may help to reduce unwanted upward bounce of breast tissue when the bra 100 is in an as-worn configuration, and further, that additional rigidity may provide strength and durability to the bra 100 structure.

Generally, the bra body 102 includes a front portion 104 (see, e.g., front portion 104 in FIG. 13) and a back portion 106. When the bra 100 is in an as-worn configuration, the front portion 104 corresponds to a ventral side (e.g., anterior) of a wearer of the bra 100. As will be apparent, the ventral side of a wearer may generally include the clavicle area, the front torso, and breast tissue, for example. And, in the as-worn configuration, the back portion 106 corresponds to a dorsal side (e.g., posterior) of a wearer of the bra 100. The dorsal side of a wearer may include, for instance, the rear shoulder area including the scapulae, and the rear torso, for example. As described herein, the front portion 104 is a front-facing portion of the bra body 102 when in an as-worn configuration, in one aspect. Additionally or alternatively, the back portion 106 is a rear-facing portion of the bra body 102.

The bra body 102 further comprises a first side or a "left" side 108 and a second side or "right" side 110. In one embodiment, the right side 110 and the left side 108 correspond to opposite sides of the bra body 102, with respect to a hypothetical midline axis 112. It will be understood that the hypothetical midline axis 112 is an imaginary or hypothetical line that generally bisects the bra body 102 into equal right and left halves, or equal first and second halves. The hypothetical midline axis 112 may run in a vertical direction, from a lower margin 103 of the bra body 102 in an upward direction towards straps (as will be described hereinafter) of the bra body 102, for example. The lower margin 103 refers to an edge or boundary of the bra 100 located opposite the right and left shoulder straps 114 and 118. As used herein, the terms shoulder straps and body straps are used interchangeably. The midline axis 112 is referred to herein to provide a simplified and clear description of the bra body 102 structure. It will further be understood that the midline axis 112 is generally parallel to or corresponds with a sagittal plane of common anatomical convention. Therefore, it will be understood by those in the relevant field that, in the as-worn configuration, the left side 108 of the bra body 102 corresponds to the left side of a wearer and the right side 110 of the bra body 102 corresponds to the right side of a wearer. It will be understood that the directional terms "left" and "right" are used conventionally herein for simplicity but may be used interchangeably with numerical terms such as first and second, for example.

Figure 3:
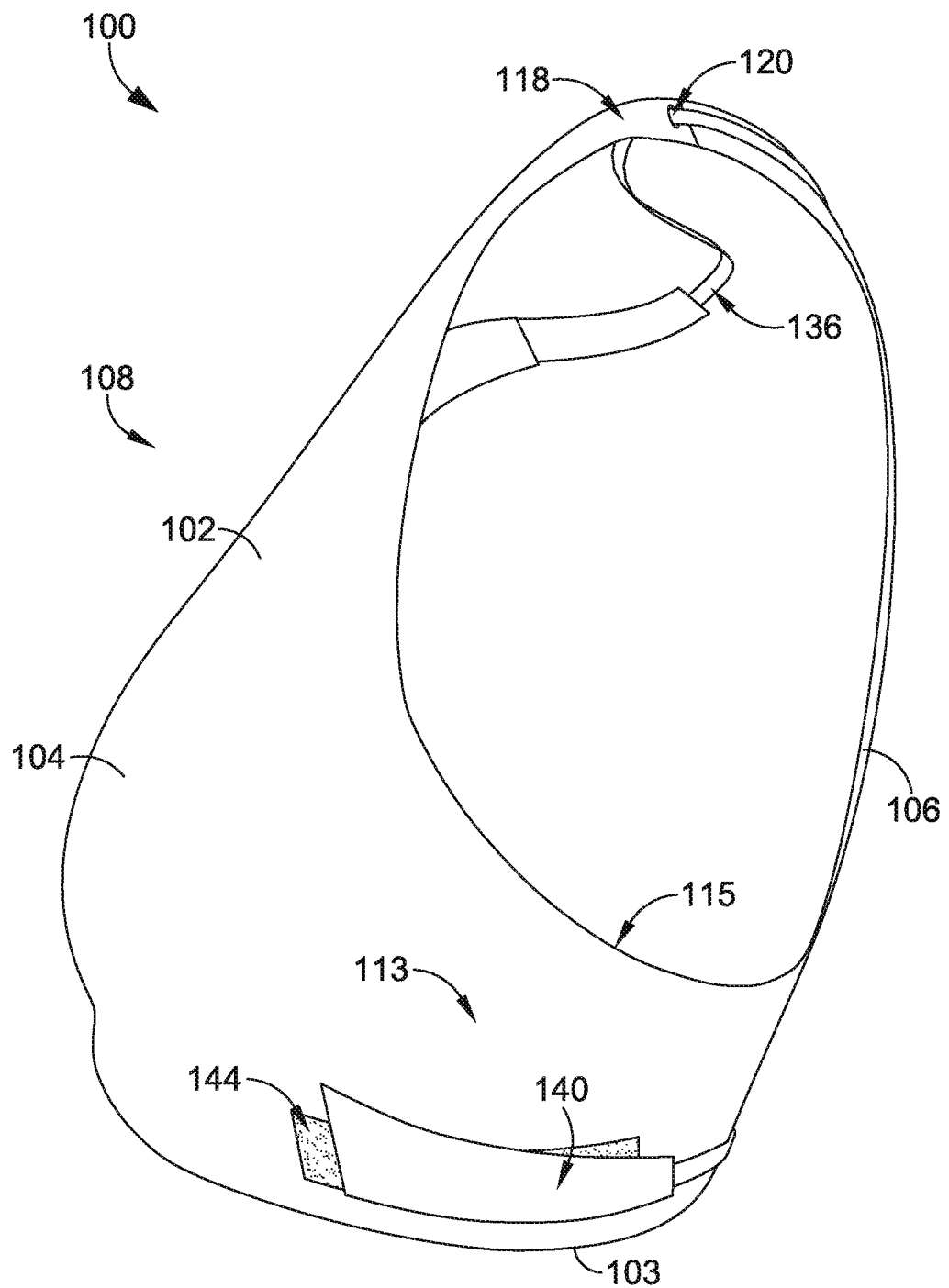
FIG. 3 depicts a side view of the bra of FIG. 1, in accordance with an aspect herein.

In aspects, the bra body 102 includes a right underarm area 111 and a left underarm area 113, with the left side 108 including the left underarm area 113 and the right side 110 including the right underarm area 111. An underarm area may be located between the front portion 104 and the back portion 106. In one aspect, an underarm area bridges or spans the bra body 102 where the front portion 104 transitions into the back portion 106. In one aspect, an underarm area generally refers to a portion of the bra body 102 structure that corresponds to and generally is located underneath an opening configured to receive an appendage (e.g., an arm) of a wearer when the bra 100 is in an as-worn configuration. For example, at FIG. 3, a side view of the bra of FIG. 1 is presented in accordance with an aspect herein, with a left underarm area 113 clearly illustrated. With respect to the midline axis 112, an underarm area may be positioned to the right and/or left outermost position relative to the midline axis 112 as allowed by the bra body 102 structure itself.

In a further aspect, the left underarm area 113 is defined by a left lateral edge 115 of the bra body 102. The left lateral edge 115 forms an edge of the left side 108 of the bra body 102. The left lateral edge 115 generally corresponds to at least a portion of an edge along, or forming, an opening that accommodates the left arm when the bra 100 is in an as-worn configuration. Similarly, the right underarm area 111 is defined by a right lateral edge 117 of the right side 110 of the bra body 102, in one aspect. The right lateral edge 117 corresponds to at least a portion of an edge along, or forming, an opening configured to receive the right arm when the bra 100 is in an as-worn configuration, for example. The term "lateral" is used herein with respect to the midline axis 112.

With continued reference to FIG. 1, the bra body 102 includes a right shoulder strap 114 with a first aperture 116 and a left shoulder strap 118 with a second aperture 120. The right shoulder strap 114 is placed on the right side 110 of the bra body 102, and the left shoulder strap 118 is placed on the left side 108 of the bra body 102, with the right and left shoulder straps 114 and 118 being non-adjustable straps, in one exemplary aspect. Alternatively, the right and left shoulder straps 114 and 118 may comprise adjustable straps. In another aspect, where each of the right and left shoulder straps 114 and 118 include distinct front and back sections connected to one another, at least a portion of the right and left shoulder straps 114 and 118 may be adjustable, for example, by tightening the adjustable section with a slide. The right and left shoulder straps 114 and 118 run from the front portion 104 to the back portion 106 in order to connect the front portion 104 to the back portion 106. As such, the front portion 104 may be coupled to at least a first end of the right shoulder strap 114 and at least a first end of the left shoulder strap 118, while in a further aspect, the back portion 106 may be coupled to at least a second end of the right shoulder strap 114 and at least a second end of the left shoulder strap 118.

In some aspects, the first aperture 116 of the right shoulder strap 114 and the second aperture 120 of the left shoulder strap 118 may comprise openings in the fabric and/or materials comprising the right and left shoulder straps 114 and 118 of the bra body 102. Exemplary openings may comprise a slit-type opening, an oval-shaped opening, a circular opening, and/or any shape or type of opening (e.g., an eyelet, a buttonhole, a grommet) that is configured to accommodate and position a harness strap used for adjusting the bra 100, as will be described hereinafter. The first aperture 116 and second aperture 120 may be created with any number of exemplary manufacturing techniques, for example, laser-cutting and die cutting. In another aspect, the first aperture 116 and second aperture 120 are formed by gaps in the weave or knit of the fabric and/or materials of the bra body 102. It will be understood that any number and kind of apertures may be present in the right and left shoulder straps 114 and 118 and as such are considered to be within the scope of this disclosure.

The first aperture 116 and the second aperture 120 are generally positioned near the first ends of the right and left shoulder straps 114 and 118. To put it another way, the first aperture 116 and the second aperture 120 may be positioned nearer the front portion 104 than the back portion 106. In other exemplary aspects, the first and second apertures 116 and 120 may be positioned nearer the back portion 106 than the front portion 104, or at an intermediate or midway position between the front portion 104 and the back portion 106. In one example, the first aperture 116 and the second aperture 120 may be positioned at similar locations on the right and left shoulder straps 114 and 118, although they may also assume a staggered orientation with respect to one another such that one aperture is positioned nearer the front portion 104 than the other aperture.

In some aspects, the first aperture 116 may be located at an apex and/or within an apex region of the right shoulder strap 114. The placement of an aperture within an apex region of a corresponding strap may stabilize and retain a harness strap during adjustment of the bra 100 via the adjustable support harness system. Generally, an apex region refers to an area of a strap that corresponds to the shoulder top of a wearer when the bra 100 is in an as-worn configuration with the apex region determined vertically with respect to the midline axis 112. For example, an apex and/or apex region may refer to a portion of a corresponding strap that connects the front portion 104 to the back portion 106 such that when the bra 100 is in an as-worn configuration, the apex and/or apex region of a corresponding strap is generally configured to contact and/or "rest" upon a wearer's shoulders. Similarly, the second aperture 120 may be placed at an apex and/or within an apex region of the left shoulder strap 118.

In exemplary aspects, the back portion 106 of the bra body 102 may comprise one or more pair of maintainers configured to receive and retain harness straps for adjusting the bra 100 using the adjustable support harness system. To put it another way, a maintainer is a feature useable to anchor a harness strap to the bra body 102. As used herein, a "maintainer" may be any structure or fitting, integrated with or coupled to the bra body 102, that redirects a tensional force, such as a force applied by or to a harness strap. In one example, a maintainer may take the form of an aperture in the bra body 102 or a fabric panel thereof through which a harness strap may be passed. In another example, a maintainer may comprise a length of material having two terminal ends that are each attached to the bra body 102, such that a harness strap, for example, may be passed under a remaining unattached portion of the material. In some aspects, the maintainers may be permanently attached or non-permanently attached to the bra body 102. Examples of attachment include use of adhesives, heat bonding, stitching, embedding between fabric layers, and/or knotting.

The maintainers described herein may form one or more sets of maintainers, one or more pairs of maintainers, and/or a combination thereof. As will be understood, the back portion 106 may include one or more maintainers, one or more pairs of maintainers, one or more sets of maintainers, or a combination thereof, such that the number, placement, location, type, or kind of maintainers depicted in the illustrative figures herein are examples only and should not be construed as limiting. For example, although three pairs of maintainers are depicted in FIG. 1, it will be understood that the bra 100 may include only one pair of maintainers, for example.

In one aspect, the back portion 106 includes a first pair of maintainers. In a further aspect, the back portion 106 additionally includes a second pair of maintainers. In yet a further aspect, the back portion 106 also includes a third pair of maintainers. Generally, a pair of maintainers comprises a right maintainer that corresponds to the right side 110 and a left maintainer that corresponds to the left side 108. In one aspect, the first pair of maintainers includes a right maintainer 122A and a left maintainer 122B, the second pair of maintainers includes a right maintainer 124A and a left maintainer 124B, and the third pair of maintainers includes a right maintainer 126A and a left maintainer 126B, as shown in FIG. 1. Generally, a right maintainer is placed opposite a left maintainer with respect to the midline axis 112.

The bra 100 further includes a liner or cup liner 128, as shown in FIG. 1. As used herein, the term "cup liner" should not be construed as limiting, but rather is merely descriptive of a particular aspect of the adjustable harness system as used in the bra 100 pictured. However, it will be understood that the liner (e.g., cup liner) may not include separate or distinct bra-type cups, but rather, may be a continuous or molded liner form that provides bust support, for example. As used herein, the term "cup" refers to a structure that provides support for breast tissue and the term is not limited to the plain and ordinary meaning. And it will be understood that a liner of the adjustable harness system may be included in other garments such as shirts and swimwear, for example, to provide bust support with or without distinct cup forms. As such, the terms "cup" and "cup liner" may be used interchangeably with section, panel, portion, or half, for example, to refer to part of the liner.

The cup liner 128 includes a right harness strap 134 coupled to a right liner cup 130 and a left harness strap 136 coupled to a left liner cup 132. In some aspects, each harness strap may be coupled to a respective first section or second section of a liner, for example. The right and left harness straps 134 and 136 may pass through the first and second apertures 116 and 120 of the right and left shoulder straps 114 and 118, respectively, and are further used in tandem with the maintainers of the bra body 102 to at least provide an adjustment to an amount of support provided by the right liner cup 130 and the left liner cup 132. Accordingly, the right and left harness straps 134 and 136 may be adjusted independently from the right and left shoulder straps 114 and 118 using a right tab 138 and/or left tab 140. The right tab 138 comprises a terminal portion of the right harness strap 134, and the left tab 140 comprises a terminal portion of the left harness strap 136, in one aspect. In a further aspect, the right tab 138 is configured to be coupled to a right attachment element 142, while the left tab 140 is configured to be coupled to a left attachment element 144 of the bra body 102. At FIG. 1, the right and left tabs 138 and 140 are shown coupled to the right and left attachment elements 142 and 144, at least a portion of which are visible. The right and left harness straps 134 and 136 are independently adjustable by using the right and left tabs 138 and 140 to pull or release the right and left harness straps 134 and 136 through the maintainers of the back portion 106. In this way, the wearer may independently adjust the right and left tabs 138 and 140 to adjust the right and left harness straps 134 and 136 through the maintainers of the back portion 106 in order to create a customized fit of the bra 100 via the adjustable support harness system. And the wearer may adjust how much of the right and left tabs 138 and 140 overlay the right and left attachment elements 142 and 144. It will be understood that the right tab 138, the left tab 140, the right attachment element 142, and the left attachment element 144 may be any size or shape, and the exemplary depictions of the bra 100 are illustrative in nature only and should not be construed as limiting.

Returning to the back portion 106, the right and left maintainers of each pair and/or set may be placed similarly to one another and with respect to the midline axis 112. Generally, a right and left maintainer of the same pair may be located at any distance from the midline axis 112, as measured perpendicular to the midline axis 112. A right and left maintainer of the same pair may be placed equidistant to a midline axis 112, measured perpendicular to the midline axis 112, for example. Alternatively, the right and left maintainer of the same pair may be placed at different distances from the midline axis 112. Continuing, a right and left maintainer of the same pair may be similarly placed lengthwise, as measured along the midline axis 112, starting from the lower margin 103 and measuring in an upward direction towards the apex region of the right and left shoulder straps 114 and 118. For example, right and left maintainers of each pair may be placed the same lengthwise distance as measured from the lower margin 103 along the midline axis 112, in some aspects.

The placement of maintainers and/or maintainer pairs as measured perpendicular to the midline axis 112 may act to help reduce collapse of the bra body 102 and/or the right and left shoulder straps 114 and 118 when adjusting the bra 100 using the adjustable support harness system. Additionally or alternatively, the placement of maintainers and/or maintainer pairs as measured lengthwise with respect to the midline axis 112 may act to reduce collapse when adjustments are made using the adjustable support harness system. At a high level, collapse refers to a shifting movement of the right and left shoulder straps 114 and 118 inward toward the midline axis 112. For example, the right maintainer 122A of the first pair may be placed at a first position and the left maintainer 122B may be placed at a second position. The first position and second position of the right maintainer 122A and the left maintainer 122B may facilitate the distribution of tensional force during adjustment of the bra 100, so that collapse of the bra structure is reduced. The first position of the right maintainer 122A may be a first distance from the midline axis 112, as measured perpendicular to the midline axis 112. The second position of the left maintainer 122B may also be a first distance from the midline axis 112, as measured perpendicular to the midline axis 112, such that the first position and the second position are the same distance from the midline axis 112. In an alternative example, the first and second positions are located at different distances from the midline axis 112, as measured perpendicular to the midline axis 112.

Additionally or alternatively, the first position of the right maintainer 122A may be placed at a first lengthwise distance, and the second position of the left maintainer 122B may also be placed at a first lengthwise distance, such that the location of the right and left maintainers 122A and 122B at the back portion 106 are the same in this regard. In an alternative example, the first and second positions are placed at different lengthwise distances. The lengthwise distances of the first and second positions may be purposefully chosen to reduce collapse of the bra structure during adjustment.

Additionally or alternatively, the right maintainer 124A of the second pair may be placed at a third position. The third position may be placed at a second lengthwise distance. The left maintainer 124B of the second pair may be placed at a fourth position, where the fourth position is also placed at a second lengthwise distance. In such an example, the third and fourth positions provide that the right and left maintainers 124A and 124B of the second pair are similarly located with respect to the midline axis 112, starting from the lower margin 103 and measuring in an upward direction towards the apex region of the right and left shoulder straps 114 and 118. In an alternative example, the third and fourth positions are placed at different lengthwise distances. The lengthwise distances of the third and fourth positions may be purposefully chosen to reduce collapse of the bra structure during adjustment.

In one aspect, the first and second positions of the right and left maintainers 122A and 122B of the first pair are placed above or superior to the third and fourth positions of the right and left maintainers 124A and 124B of the second pair, as measured along the midline axis 112 and with respect to the lower margin 103, such that the first and second positions of the right and left maintainers 122A and 122B of the first pair are located nearer the apex region than the third and fourth positions of the right and left maintainers 124A and 124B of the second pair, for example. And further, the third and fourth positions are located nearer the lower margin 103 than the first and second positions, in such an example. As used herein, "above" refers to location(s) of the bra 100 proximate to the apex region, whereas the term "below" refers to location(s) of the bra 100 proximate to the lower margin 103, such that when a first element is located above a second element, the first element is nearer the apex than the second element, and the second element is nearer the lower margin 103 than the first element, for example. Continuing, the first, second, third, and fourth positions of corresponding maintainers may be determined in order to reduce collapse of the bra body 102 and/or the right and left shoulder straps 114 and 118 when adjusting the bra 100 using the adjustable support harness system.

Additionally, in further aspects, the third and fourth positions of the right and left maintainers 124A and 124B of the second pair, as measured lengthwise along the midline axis 112 and with respect to the lower margin 103, are positioned above a fifth position of a right maintainer 126A and a sixth position of a left maintainer 126B of the third pair. A lengthwise measurement of the third and fourth positions of the second pair may be different than a lengthwise measurement of the fifth and sixth positions of the third pair, for example. In one example, the first pair of maintainers (e.g., right and left maintainers 122A and 122B) may be positioned above the second pair of maintainers (e.g., right and left maintainers 124A and 124B) and further, the second pair of maintainers (e.g., right and left maintainers 124A and 124B) may be placed above the third pair of maintainers (e.g., right and left maintainers 126A and 126B) as measured lengthwise with respect to the midline axis 112 and with respect to the lower margin 103. As will be understood, the positions of one or more pairs of maintainers depicted in exemplary FIG. 1 should not be construed as limiting, as the placement and lengthwise measurements of each maintainer of each pair may be adjusted or changed and still be within the scope of this disclosure.

In one example, the first pair of maintainers (e.g., right and left maintainers 122A and 122B) may be placed at a first distance measured perpendicular to the midline axis 112 and the second pair of maintainers (e.g., right and left maintainers 124A and 124B) may be placed at a second distance measured perpendicular to the midline axis 112, wherein the second distance is greater than the first distance, for example. In such an example, the first pair of maintainers (e.g., right and left maintainers 122A and 122B) may be located closer to the midline axis 112 than the second pair of maintainers (e.g., right and left maintainers 124A and 124B). In an alternative aspect, the second distance may be less than the first distance so that the second pair of maintainers (e.g., right and left maintainers 124A and 124B) is closer to the midline axis 112 than the first pair of maintainers (e.g., right and left maintainers 122A and 122B).

The placement of maintainers may be described with respect to pairs, sets, individual maintainers, maintainers of the right side 110, and/or maintainers of the left side 108. For example, the right maintainer 122A of the first pair may be located above the right maintainer 124A of the second pair, and the right maintainer 124A of the second pair may be located above the right maintainer 126A of the third pair when measured along a vertical direction of the midline axis 112. Accordingly, in such an example, the right maintainer 122A is placed vertically higher than the right maintainer 124A such that the right maintainer 122A is located nearer to the right shoulder strap 114 than the right maintainer 124A. Alternatively, the first, second, and third pairs of maintainers (e.g., right and left maintainers 122A, 122B, 124A, 124B, 126A, and 126B) may be placed in a different vertical configuration, as any number of vertical maintainer configurations may be used to interface with the harness straps of the adjustable support harness system.

In further aspects, the first pair of maintainers is positioned at and/or near a right edge 123 and a left edge 125 of the back portion 106, respectively. In one aspect, the positions of the maintainers at or near the right edge 123 and the left edge 125 may reduce collapse of the bra body 102 and/or right and left shoulder straps 114 and 118 during adjustment of the bra 100 using the adjustable support harness system.

The pairs and/or sets of maintainers may be vertically spaced apart from one another, such that each pair and/or set has a different lengthwise measurement (as previously described herein with respect to the midline axis 112 and the lower margin 103) than the other pairs or sets. In one example, a lengthwise measurement between the first pair of maintainers (e.g., right and left maintainers 122A and 122B) and the second pair of maintainers (e.g., right and left maintainers 124A and 124B), as measured in a vertical direction with respect to the midline axis 112, is greater than a lengthwise measurement between the second pair of maintainers (e.g., right and left maintainers 124A and 124B) and the third pair of maintainers (e.g., right and left maintainers 126A and 126B). Alternatively, the lengthwise measurement or vertical spacing between one or more pairs and/or sets of maintainers may be the same. Moreover, right or left maintainers of the same or different pairs and/or sets of maintainers may be horizontally and/or vertically spaced apart from other right or left maintainers, with respect to the midline axis 112.

Figure 2:
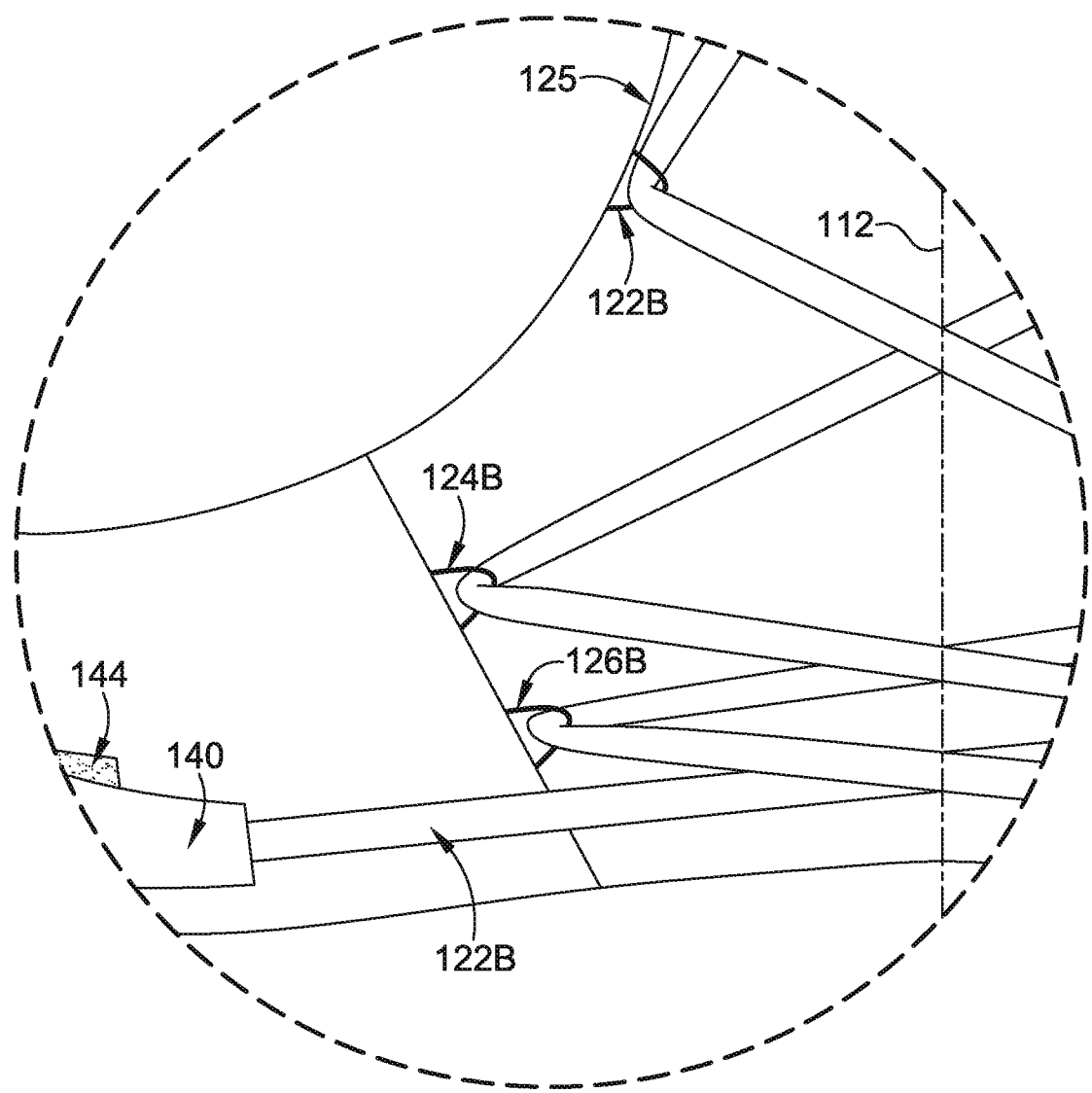
FIG. 2 depicts an enlarged view of the bra of FIG. 1, in accordance with an aspect herein.

Turning next to FIG. 2, an enlarged view of the bra of FIG. 1 includes the left maintainer 122B of the first pair of maintainers, the left maintainer 124B of the second pair of maintainers, and the left maintainer 126B of the third pair of maintainers, each maintainer placed at a different position on the left side 108. The positions of the left maintainers 122B, 124B, and 126B are different distances from the midline axis 112 and as measured perpendicular to the midline axis 112. In an alternative configuration, the positions of the left maintainers 122B, 124B, and 126B may be the same distance from the midline axis 112 and as measured perpendicular to the midline axis 112. In the illustrative aspect of FIG. 2, the left maintainer 122B of the first pair of maintainers, the left maintainer 124B of the second pair of maintainers, and the left maintainer 126B of the third pair of maintainers are positioned differently on the left side 108 as measured in a horizontal direction with respect to the midline axis 112. In one example, a first, horizontal distance measured from the midline axis 112 to the left maintainer 122B of the first pair of maintainers is less than a second, horizontal distance measured from the midline axis 112 to the left maintainer 124B of the second pair of maintainers. And in another example, a distance measured from the midline axis 112 to the left maintainer 124B of the second pair of maintainers is greater than another distance measured from the midline axis 112 to the left maintainer 126B of the third pair of maintainers.

It will be understood that the maintainer configurations illustrated in FIGS. 1 and 2, including the number, vertical placement, horizontal placement, and relative placement of maintainers, should not be construed as limiting as other configurations, placements, and/or distances are considered to be within the scope of this disclosure. The configuration, placement, and/or distances of each maintainer in each set and/or pair may be determined in order to increase or enhance the adjustment capabilities of the adjustable support harness of the bra 100, and to provide a wearer with improved comfort, durability, and support. As such, the varied configuration, placement, and/or distances of maintainers described herein may provide for a same-side adjustment feature of the harness straps of the adjustable support harness system. In further aspects, the back portion 106 includes one or more sets of maintainers, wherein each set of maintainers comprises multiple pairs of right and left maintainers. Additionally, any number of sets of maintainers, pairs of maintainers, additional maintainers, and types of maintainer structures are considered to be within the scope of this disclosure.

Figure 4:
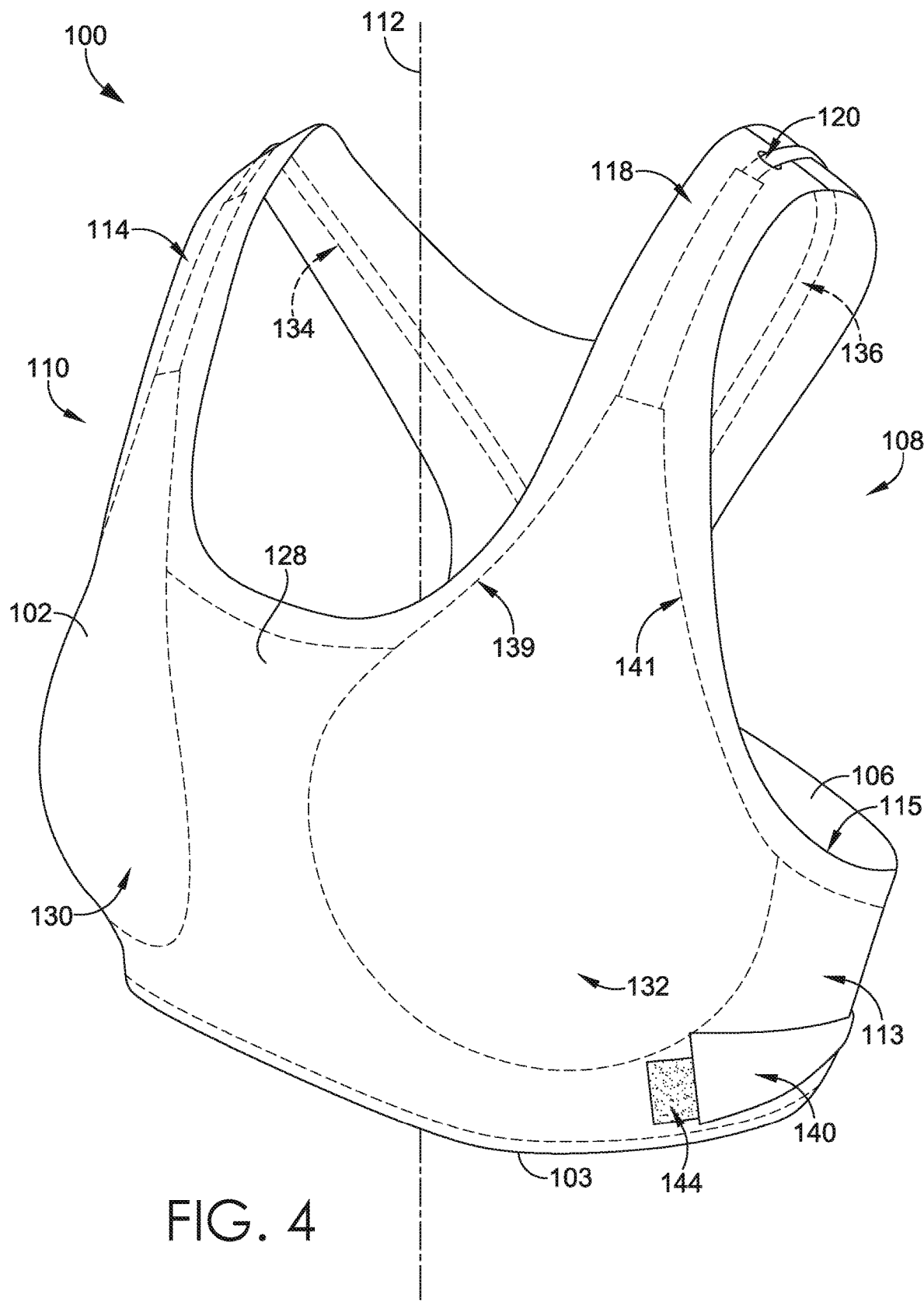
FIG. 4 depicts a front, perspective view of the bra of FIG. 1, in accordance with an aspect herein.

Continuing with FIG. 4, one aspect of the bra body 102 includes a cup liner 128 positioned at the interior of the bra body 102. As indicated, the cup liner 128 may be configured to contact the skin of a wearer when the bra 100 is in an as-worn configuration. Aspects of the cup liner 128 include a right liner cup 130 and a left liner cup 132, and may be constructed from one or more panels of one or more materials and/or fabrics. Generally, the cup liner 128 is configured to be positioned at an interior of the bra body 102, as indicted by dashed lines. The cup liner 128 helps to form a supportive layer of the bra 100, with the right and left liner cups 130 and 132 providing bra cup structures configured to hold, secure, and/or support breast tissue when the bra 100 is in an as-worn configuration. As shown in the example of FIG. 4, the right liner cup 130 corresponds to the right side 110 of the bra body 102, while the left liner cup 132 corresponds to the left side 108 of the bra body 102.

Figure 5:
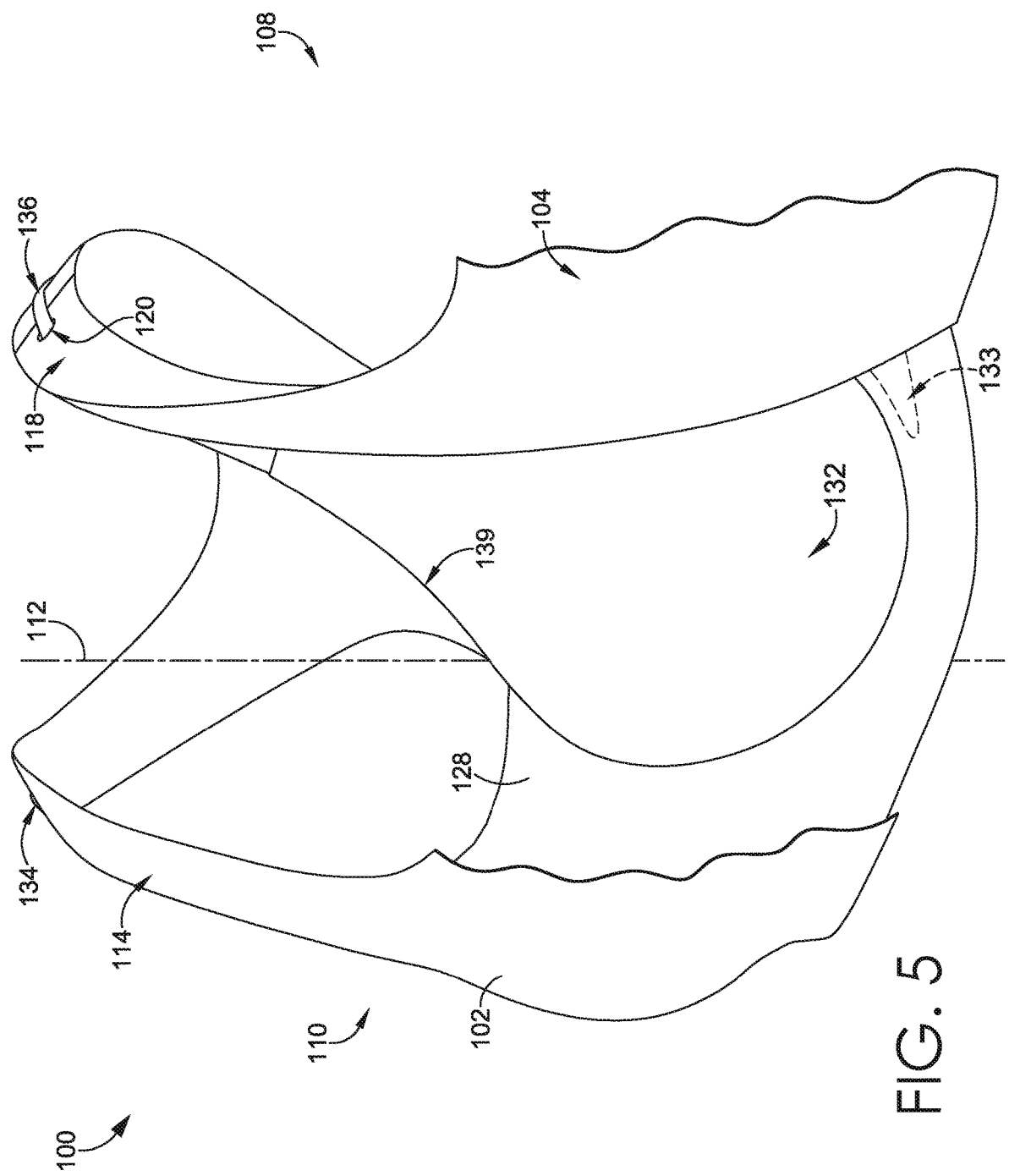
FIG. 5 depicts a front, perspective view of the bra of FIG. 1 with a portion of the bra body removed, in accordance with an aspect herein.
Figure 6:
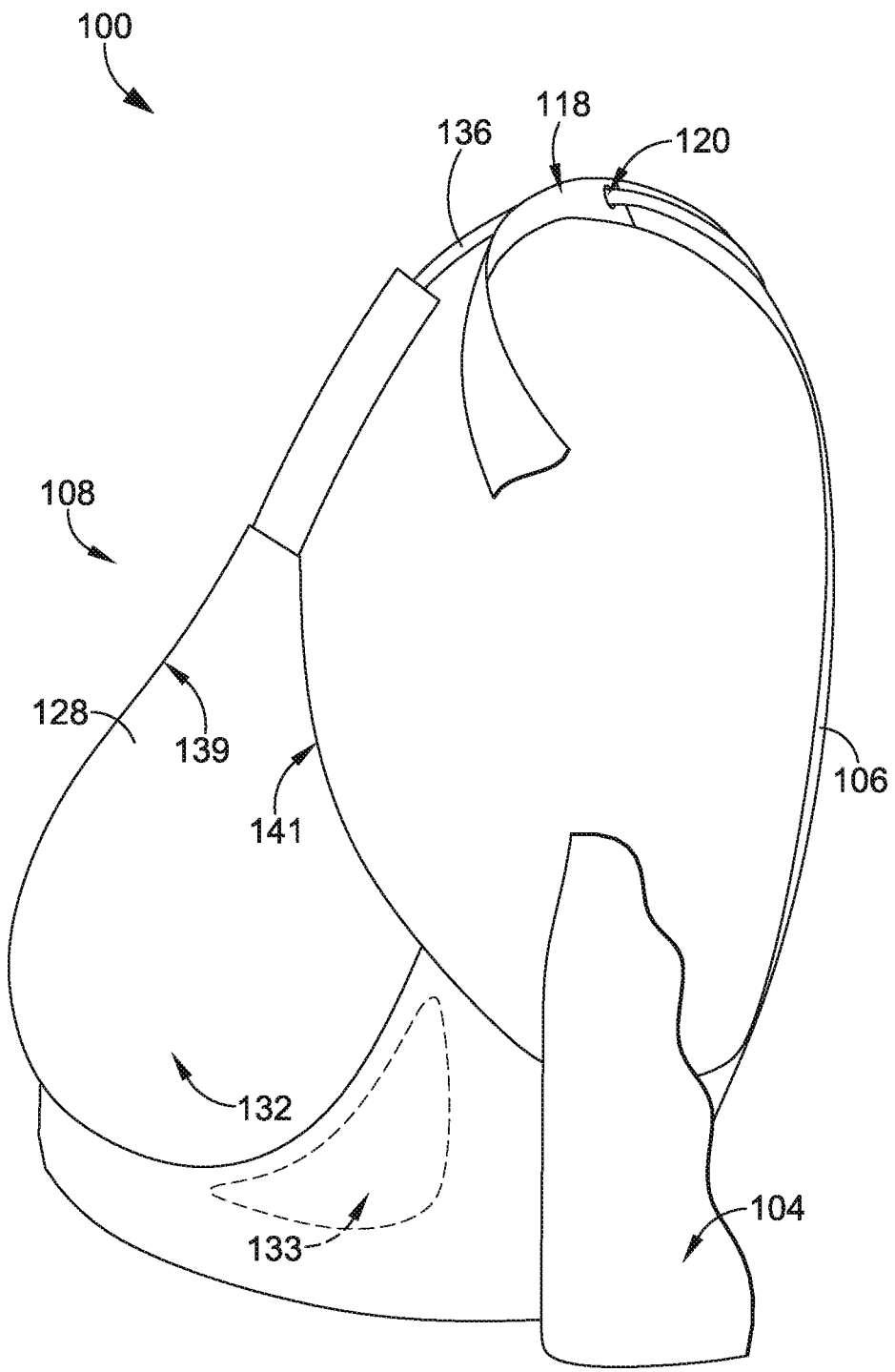
FIG. 6 depicts a side view of the bra of FIG. 1 with a portion of the bra body removed, in accordance with an aspect herein.
Figure 7:
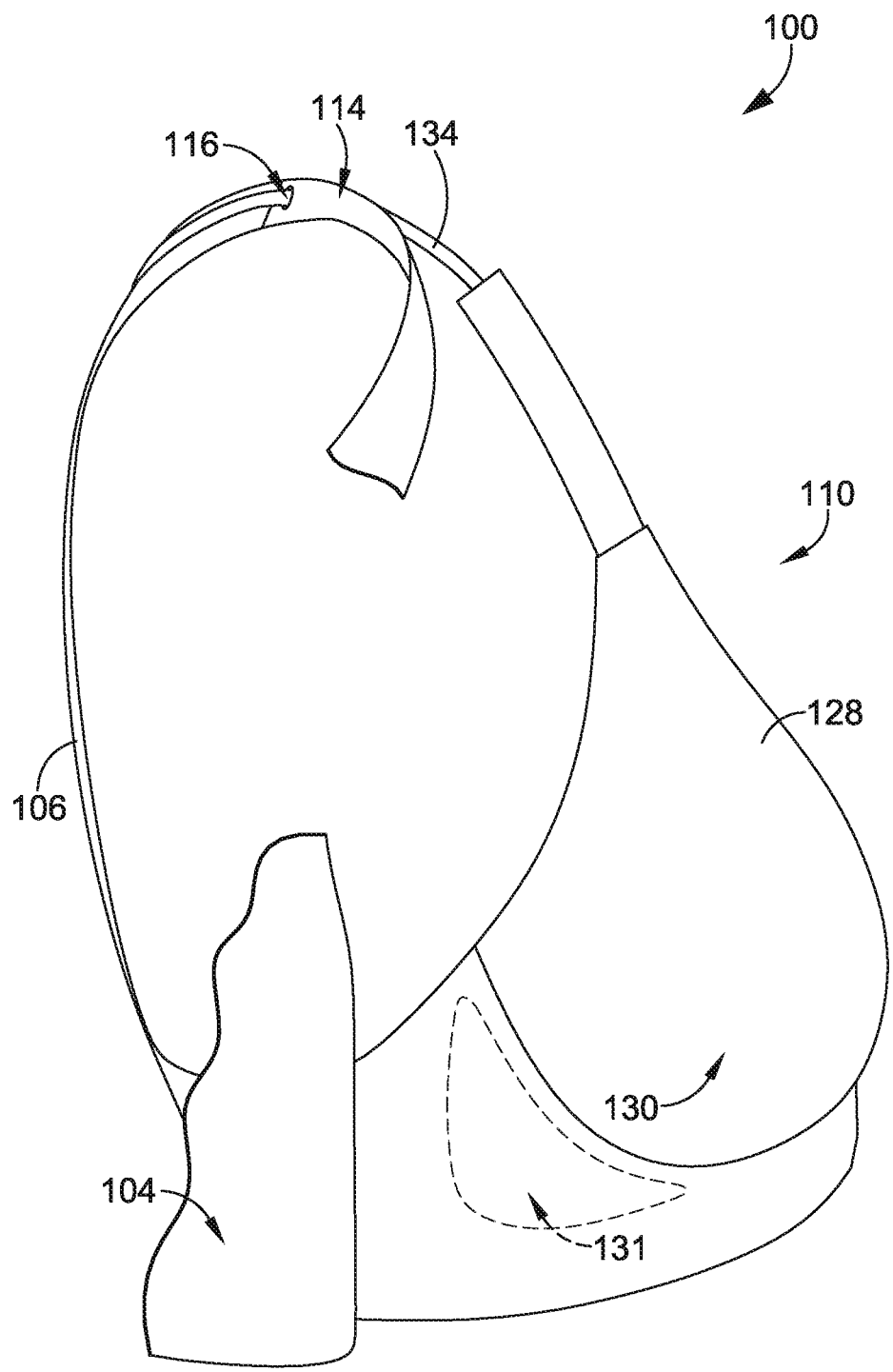
FIG. 7 depicts another side view of the bra of FIG. 1 with a portion of the bra body removed, in accordance with an aspect herein.

Additional supportive functions of the cup liner 128 are further illustrated in FIGS. 5-7. FIG. 5 depicts a perspective view of the bra 100 of FIG. 1 with a portion of the bra body 102 removed to reveal the cup liner 128. Similarly, FIG. 6 depicts a left side view of the bra 100 of FIG. 1 with a portion of the bra body 102 removed, while FIG. 7 depicts a right side view of the bra 100 of FIG. 1 with a portion of the bra body 102 removed. As revealed in FIGS. 5-7, the cup liner 128 may include a right support pad 131 and a left support pad 133, each corresponding to a respective side. The right support pad 131 is further placed adjacent the right liner cup 130, in some aspects. For example, the right support pad 131 may not be integrated with the right liner cup 130, but placed alongside the right liner cup 130. Similarly, the left support pad 133 may be located adjacent the left liner cup 132. Generally, the right and left support pads 131 and 133 include one or more layers of foam materials and/or padding materials which, as positioned, move or "push" breast tissue toward the front portion 104 when the bra 100 is in an as-worn configuration. As such, the right and left support pads 131 and 133 facilitate movement of breast tissue into respective right and left liner cups 130 and 132 and aid in holding said tissue therein. With breast tissue placed in the cup liner 128, the bra 100 may be adjusted using the adjustable support harness system. In further aspects, the right and left support pads 131 and 133 are placed and/or sealed between one more layers of fabric comprising the cup liner 128. The right support pad 131 and the left support pad 133 may be embedded between two or more layers of material or fabric that comprise the cup liner 128 and/or the bra body 102, in some aspects. And the right support pad 131 and the left support pad 133 may extend inwardly from the surface plane of the cup liner 128 (e.g., extend toward the body of the wearer when the bra 100 is in an as-worn configuration). By extending inward, the right support pad 131 and the left support pad 133 may help to push breast tissue toward the front portion 104 and away from the right underarm area 111 and the left underarm area 113, for example.

As illustrated in FIGS. 4-7, the cup liner 128 further comprises a right harness strap 134 coupled to the right liner cup 130 and a left harness strap 136 coupled to the left liner cup 132. The right and left harness straps 134 and 136 are employed in tandem with the maintainers of the bra body 102 to at least provide an adjustment to an amount of support provided by the right liner cup 130 and the left liner cup 132 of the cup liner 128. The right and left harness straps 134 and 136 may comprise footwear-type laces, round lacing material, flat-type or planar lacing material, strings, ribbons, braided cords, knit cords, woven cords, nylon cords, neoprene, and/or one or more other materials. Exemplary materials may have a low coefficient of friction to promote the ability of the right and left harness straps 134 and 136 to slide through the first and second apertures 116 and 120. Additionally or alternatively, exemplary materials may exhibit a lower modulus of elasticity that imbues the right and left harness straps 134 and 136 with stretch. As such, the right and left harness straps 134 and 136 may be made from any material capable of passing through the first and second apertures 116 and 120 of the harness structure.

In one aspect, the right harness strap 134 is coupled to the right liner cup 130, such as by coupling a first end of the right harness strap 134 to an apex region of the right liner cup 130, and/or to another portion corresponding to an upper stretch region of the right liner cup 130. As used herein, "coupled to" and "affixed to" refers to permanent and/or non-permanent coupling, and the terms should not be construed as limiting. Exemplary types of coupling or affixing include stitching, serging, gluing, heat fixing, heat bonding, pressure bonding, and/or other techniques or combinations thereof. Additionally, the left harness strap 136 is coupled to the left liner cup 132, such as by coupling a first end of the left harness strap 136 to an apex region of the left liner cup 132, determined vertically with respect to the midline axis 112, and/or to another portion corresponding to an upper stretch region of the left liner cup 132.

The right harness strap 134 is configured to pass through the first aperture 116 of the right shoulder strap 114, while the left harness strap 136 is configured to pass through the second aperture 120 of the left shoulder strap 118, in one aspect. The right and left harness straps 134 and 136 are generally configured to move freely or travel through the first and second apertures 116 and 120 of the right and left shoulder straps 114 and 118, respectively. In some aspects, the right and left harness straps 134 and 136 are independently adjustable via the harness system. For instance, the right and left harness straps 134 and 136 are adjustable by sliding through respective first and second apertures 116 and 120, while the right and left shoulder straps 114 and 118 remain stationary. Accordingly, the right and left harness straps 134 and 136 may be adjusted independently from the right and left shoulder straps 114 and 118.

When the harness system is used to adjust the bra 100, the right and left harness straps 134 and 136 experience tensioning forces based on pulling and releasing each strap. During this action, the first and second apertures 116 and 120 may act to maintain the harness strap position of the right and left harness straps 134 and 136, according to some aspects. For instance, the first and second apertures 116 and 120 may deter the right and left harness straps 134 and 136 from becoming displaced during adjustment, and from slipping or falling off the shoulders when the bra 100 is adjusted in an as-worn configuration. Therefore, the first and second apertures 116 and 120 may help to position the right and left harness straps 134 and 136 at or within the apex region such that the right and left harness straps 134 and 136 lie adjacent to the right and left shoulder straps 114 and 118 generally along their length.

After passing through the first and second apertures 116 and 120, respectively, the right and left harness straps 134 and 136 are configured to cross one another at the back portion 106, as illustrated in exemplary FIG. 1. Generally, the right harness strap 134 is configured to cross over the left harness strap 136 at the midline axis 112. In another example, the left harness strap 136 is configured to cross over the right harness strap 134 at the midline axis 112.

After crossing the left harness strap 136, the right harness strap 134 is configured to pass through at least one maintainer of each of the first, second, and third pairs of maintainers, in one aspect. And after crossing the right harness strap 134, the left harness strap 136 is configured to pass through at least one maintainer of each of the first, second, and third pairs of maintainers, in another aspect. In some aspects, the right and left harness straps 134 and 136 crisscross back and forth over the midline axis 112 and the back portion 106 of the bra body 102. In further aspects, the right and left harness straps 134 and 136 crisscross one another more than once at the back portion 106 of the bra body 102. In a further aspect, the right harness strap 134 is configured to sequentially pass through a left maintainer 122B of the first pair of maintainers, a right maintainer 124A of the second pair of maintainers, and a left maintainer 126B of the third pair of maintainers. Additionally, the left harness strap 136 is configured to sequentially pass through a right maintainer 122A of the first pair of maintainers, a left maintainer 124B of the second pair of maintainers, and a right maintainer 126A of the third pair of maintainers, in another further aspect, although other crossing patterns are contemplated herein.

The crisscrossing nature of the right and left harness straps 134 and 136 through a series of maintainers forms a portion of the adjustable support harness system. The number and placement of the maintainers may further impact the adjustable support harness system. It will be understood that alternative configurations for "lacing" the right and left harness straps 134 and 136 through various maintainers are considered to be within the scope of this disclosure and the configuration depicted in the exemplary figures herein should not be construed as limiting.

Continuing, the right harness strap 134 terminates in a right tab 138 and the left harness strap 136 terminates in a left tab 140, as depicted in exemplary FIG. 1. The left tab 140 is additionally visible in FIG. 3. The right and left tabs 138 and 140 may be used to adjust the right and left harness straps 134 and 136. The right and left tabs 138 and 140 are configured to be coupled to at least a portion of the bra body 102. In some aspects, the right tab 138 is configured to be coupled to a right attachment element 142 of the bra body 102, while the left tab 140 is configured to be coupled to a left attachment element 144 of the bra body 102.

In one aspect, the right and left attachment elements 142 and 144 are located at an exterior of the bra body 102. The right attachment element 142 is placed at an exterior surface of the bra body 102 on the right side 110, while the left attachment element 144 is placed at an exterior surface of the bra body 102 on the left side 108, in one aspect. In further aspects, the right and left attachment elements 142 and 144 are placed at or near the right underarm area 111 and the left underarm area 113 of the bra body 102. It will be understood that an attachment element and/or attachment mechanism may include an area having one or more fasteners (e.g., snaps, buttons, hook-and-loop fasteners, ties, etc.), such that the attachment element includes a variety of different degrees or locations of attachment. Exemplary fasteners include hook-and-loop fasteners, micro hook-and-loop fasteners, and fasteners formed integrally from the knit or weave of the fabric itself. In some aspects, the fasteners may be nearly invisible or indistinguishable to the naked eye and might also be indistinguishable to the touch from other portions of a garment lacking such fasteners. As such, the right and left attachment elements 142 and 144 provide for a range of attachment elements such that the right and left tabs 138 and 140 may be placed at several different positions within the right and left attachment elements 142 and 144. This range provides a wearer with the ability to adjust the bra 100 by manipulating one or more of the right and left tabs 138 and 140 in order to tighten or loosen the fit of the one or more of the right and left harness straps 134 and 136 connected thereto, as is further discussed below.

Moreover, the placement of the right and left attachment elements 142 and 144 may facilitate attaching the right and left tabs 138 and 140, as said right and left tabs 138 and 140 are within a wearer's reach when the bra 100 is in an as-worn configuration. For example, a wearer may manipulate one or more of the right and left tabs 138 and 140 and determine where to couple said right and left tabs 138 and 140 to the right and left attachment elements 142 and 144. Such manipulation may tighten or loosen the fit of the right and left harness straps 134 and 136 as attached to the right and left tabs 138 and 140, and at the opposite end, as attached to the cup liner 128. Furthermore, the wearer may independently adjust the right and left tabs 138 and 140 to adjust the right and left harness straps 134 and 136 in order to create a customized fit of the bra 100 via the adjustable support harness system.

The configuration of maintainers and the configuration of the harness straps results in the tabs providing a same-side adjustment feature of the harness system of the bra 100. By manipulating the right tab 138, the right harness strap 134 is adjusted, and by manipulating the left tab 140, the left harness strap 136 is adjusted, in one aspect. Therefore, the bra 100 and harness system provides a wearer with a same-side adjustment feature. The same-side adjustment feature reduces confusion for a wearer. For example, attaching the right tab 138 to the right attachment element 142 adjusts the right harness strap 134 and the right liner cup 130. Further, attaching the left tab 140 to the left attachment element 144 adjusts the left harness strap 136 and the left liner cup 132. In some aspects, the same-side adjustment feature of the adjustable support harness system is produced by specifically configuring a number of times for each harness strap to cross the midline axis 112.

For example, as shown in the exemplary aspect of FIG. 1, the right harness strap 134 crosses the midline axis 112 four times, and the left harness strap 136 crosses the midline axis 112 four times. In the rear of the bra 100, in exemplary aspects, each of the right and left harness straps 134 and 136 cross the midline axis an even number of times. As such, the harness-strap-and-maintainer configuration having even number of midline axis 112 crossings produces a same-side adjustment feature, with the right tab 138 coupling to the right attachment element 142 on the right side 110 of the bra body 102 to adjust the right harness strap 134 and the right liner cup 130, and the left tab 140 coupling to the left attachment element 144 on the left side 108 of the bra body 102 to adjust the left harness strap 136 and the left liner cup 132. In some aspects, a same-side adjustment of the right liner cup 130 and the left liner cup 132 may refer to a stretching force applied to a material of the respective cup liner in response to adjustment by the corresponding right harness strap 134 and left harness strap 136, as described in further detail below.

Figure 8:
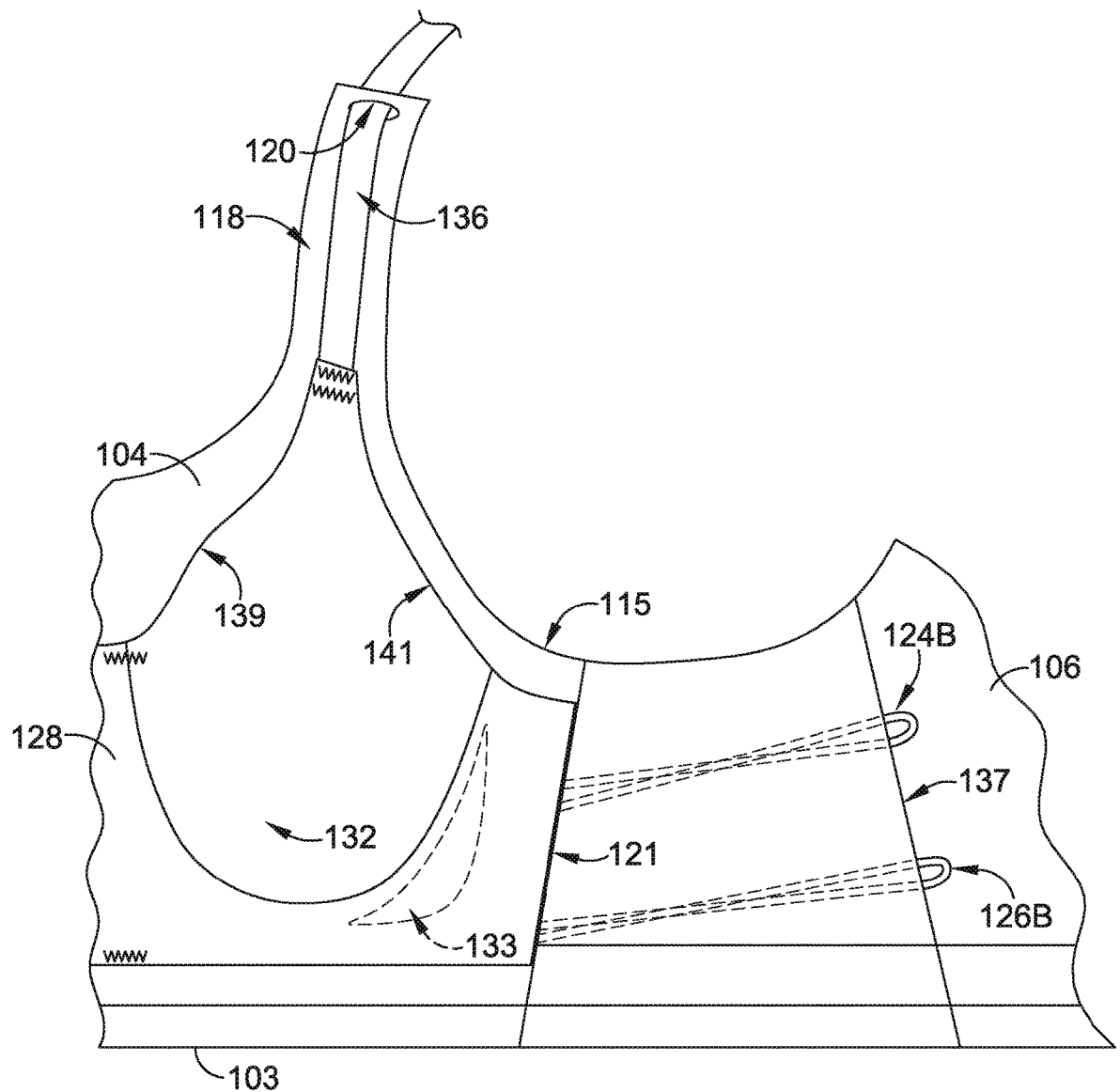
FIG. 8 depicts an internal view of the left side of the bra of FIG. 1, in accordance with an aspect herein.

Turning now to FIG. 8, a deconstructed view of the left side of the bra 100 of FIG. 1 depicts an interconnected relationship between the bra body 102, the cup liner 128, the harness straps (such as left harness strap 136), the apertures (such as second aperture 120), and the maintainers (such as left maintainers 124B and 126B) in the construction of the bra 100. In the example of FIG. 8, the connection of the left liner cup 132 to the left harness strap 136, which is then threaded through a series of maintainers including left maintainer 124B, provides an exemplary illustration of the interconnectedness of the harness system.

FIG. 8 also illustrates a coupling between the cup liner 128 and the bra body 102 at least at one portion of the bra 100, such as, for example, at seam 121 and/or seam 137 of the bra body 102. In another aspect, the cup liner 128 may be coupled to the bra body 102 at one or more additional locations. For example, the cup liner 128 may be coupled to the bra body 102 at the front portion 104, the back portion 106, the left side 108, the right side 110, or a combination thereof. In another example, a portion of the bra body 102 may be coupled in a continuous manner to one or more portions of the cup liner 128. Therefore, during adjustment of the bra 100, portions of the cup liner 128 may remain unattached from the bra body 102 and move freely so that each feature of the cup liner 128 is adjusted by the adjustable harness system, moving one or more of the right and left harness straps 134 and 136 and shifting at least a portion of the cup liner 128, while the bra body 102 provides a stable and fixed structure for stabilizing the right and left tabs 138 and 140. In one such aspect, the cup liner 128 is not attached to the bra body 102 along a first upper edge 139 and a second upper edge 141 of a left liner cup 132 and/or similarly oriented upper edges of the right liner cup. During bra 100 adjustment, the right and left harness straps 134 and 136 may move through the first and second apertures 116 and 120, respectively, while pulling on the cup liner 128 causing the first and second upper edges 139 and 141 to move vertically with respect to the midline axis 112. Because the first upper edge 139 and a second upper edge 141 of the left liner cup 132 are unattached to the bra body 102, the left liner cup 132 may shift and move based on the pulling of a corresponding left harness strap 136. And, during adjustment, each of the one or more maintainers, such as left maintainers 124B and 126B, may be a coupled to a stationary portion of the cup liner 128, the bra body 102, or a combination thereof, so as to remain in a fixed location.

In FIG. 8, left maintainers 124B and 126B are attached to the bra body 102 at seam 137. In one aspect, the left maintainers 124B and 126B each comprise a length of cord embedded or secured between fabric layers such that a rounded portion of each cord is exposed at the back portion 106 to form the exposed or visible portions of the left maintainers 124B and 126B. In such an aspect, the length of cord may be affixed (e.g., stitched) to the bra body 102 at one or more locations, including seam 137 and/or seam 121. In the example of FIG. 8, left maintainers 124B and 126B remain exteriorly exposed at the back portion 106. And the remaining maintainer materials (e.g., a length of cord) extends from seam 137 to seam 121, where the remaining maintainer material is affixed to at least a portion of the cup liner 128 and/or the bra body 102, in the aspect of exemplary FIG. 8. FIG. 8 may include an optional positioning strip (not shown).

Figure 9:
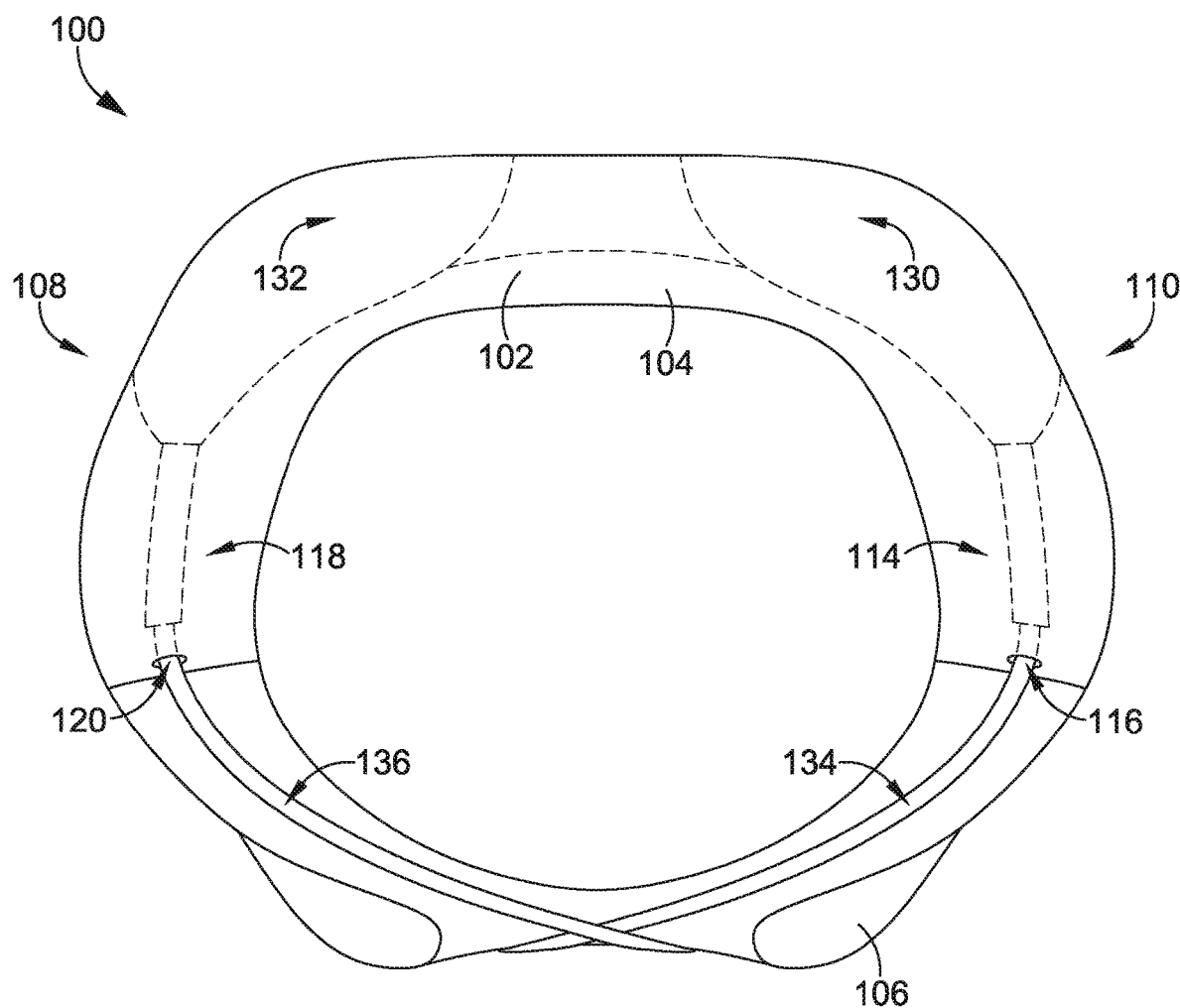
FIG. 9 depicts an overhead view of the bra of FIG. 1, in accordance with an aspect herein.

For the purposes of this discussion, it will be understood that these figures illustrate exemplary aspects and should not be construed as limiting. The bra body 102 and/or the cup liner 128 might include additional features not illustrated in the aspects depicted. At FIG. 9, an overhead view of the bra of FIG. 1 is shown in accordance with an aspect herein. In FIG. 9, the right harness strap 134 is located at the interior of the bra body 102 prior to passing through the first aperture 116, but is located at the exterior of the bra body 102 after passing through the first aperture 116. The left harness strap 136 also shifts, with respect to the bra body 102, from an interior placement to an exterior placement upon passing through the second aperture 120 of the left shoulder strap 118.

Continuing with FIG. 9, the right and left harness straps 134 and 136, after passing through corresponding first and second apertures 116 and 120 of the right and left shoulder straps 114 and 118, are laced through the maintainers of the back portion 106. The stable and/or fixed-location maintainers anchor and/or tether one or more of the right and left harness straps 134 and 136 to the back portion 106 of the bra body 102. In this way, the right and left harness straps 134 and 136, which are coupled to the right and left liner cups 130 and 132, and the right and left tabs 138 and 140, provide a flexible, movable feature that is stabilized by the right and left shoulder straps 114 and 118 and said maintainers and which enables adjusting the bra 100 using the adjustable support harness system.

Figure 11:
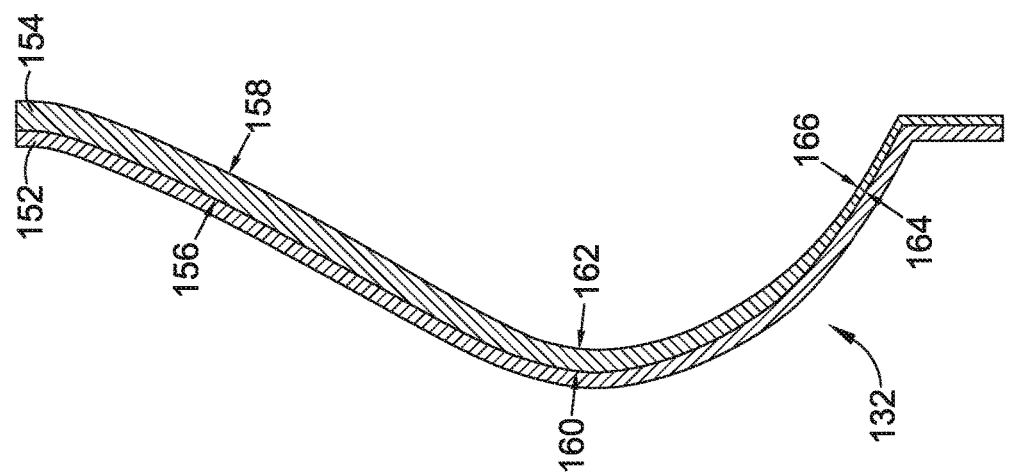
FIG. 11 depicts a cross section of the left liner cup of FIG. 10, in accordance with an aspect herein.
Figure 10:
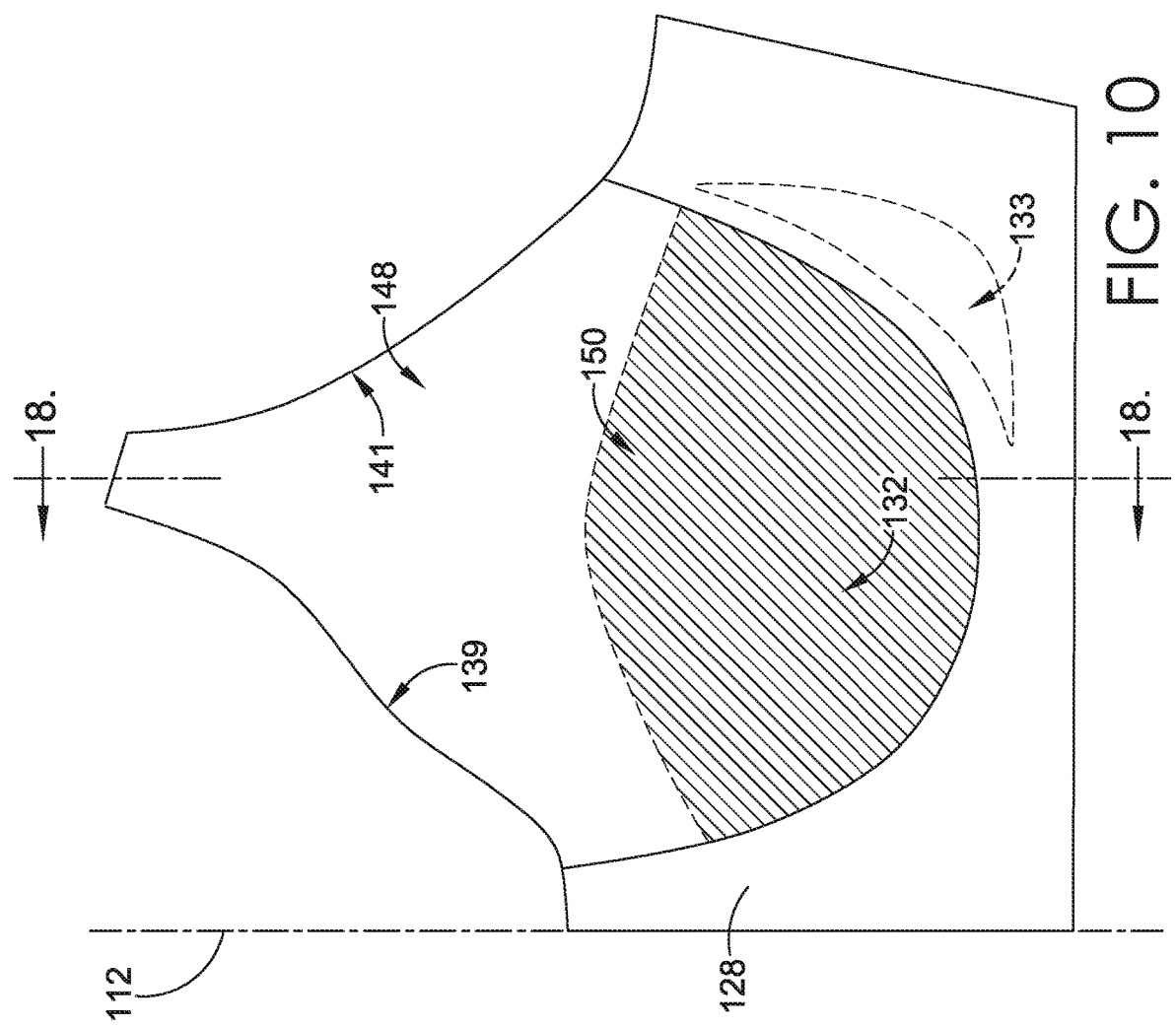
FIG. 10 depicts a front view of a left liner cup of the bra of FIG. 1, in accordance with an aspect herein.

The adjustability of the bra 100 may be further enhanced by characteristics of the cup liner 128 construction. FIG. 10 depicts a front view of a left liner cup of the bra of FIG. 1 in accordance with an aspect herein, and FIG. 11 depicts a cross section of the left liner cup of FIG. 10 in accordance with an aspect herein. The adjustable support provided by the harness system may be enhanced using zones of the right and left liner cups 130 and 132. The left liner cup 132 comprises a first zone 148 and a second zone 150, in addition to the left support pad 133. Although not shown in FIG. 10 or 11, the right liner cup 130 includes a first zone and a second zone as well. Generally, the first zone 148 and the second zone 150 are formed from the same material. However, the first zone 148 may correspond to a first molding characteristic and the second zone 150 may correspond to a second molding characteristic, in aspects. In exemplary aspects, the first zone 148 and the second zone 150 may exhibit different characteristics and/or a different degree of the same characteristic. A different molding technique, and/or a different degree of the same molding technique, may be applied to each of the first zone 148 and the second zone 150 in order to imbue said first and second zones 148 and 150 with characteristics that are not the same, or a different degree of the same characteristic.

For example, in one aspect, the first zone 148 has a first molding characteristic comprising a degree of elasticity different than the second zone 150 having a second molding characteristic of decreased elasticity, in comparison. Accordingly, the first zone 148 exhibits an increased degree of elasticity and/or stretch than the second zone 150. Other exemplary characteristics are considered to be within the scope of this disclosure, such as density, ability to expand, thickness, ability to retain shape, ability to resist distortion after wear and tear (e.g., when a fabric "stretches" out), material breathability, material air permeability, moisture-wicking properties, and the like.

In one aspect, the first zone 148 of a liner cup is located proximate to a harness strap coupled to the liner cup. The first zone 148 may abut or include an area where the harness strap is coupled to the liner cup, in another aspect. In one example, the first zone 148 is placed nearer a harness strap than the second zone 150, as measured vertically with respect to the midline axis 112. As such, manipulating a tab to adjust the bra via the harness system moves a corresponding harness strap, and the harness strap pulls upward on a corresponding left or right liner cup of the cup liner 128. The upward force or pull experienced at the liner cups cause the first zone 148 of the manipulated liner cup to move and/or stretch more than the second zone 150. For example, the left harness strap may be pulled to generally apply force to the first zone 148 of the left liner cup 132, while the right harness strap may be pulled to generally apply force to the first zone of the right liner cup. Further, in some aspects, the first zone 148 stretches to accommodate the force applied by each harness strap. While the first zone 148 stretches, the second zone 150 is also pulled upward, measured vertically with respect to the midline axis 112. However, because the second zone 150 is less elastic than the first zone 148, the second zone 150 shifts upward a lesser distance than the first zone 148 is stretched upward.

At FIG. 11, a first layer 152 and a second layer 154 have been molded together to form the left liner cup 132 of FIG. 10. In aspects, the first layer 152 comprises stretch foam and the second layer 154 comprises spacer material(s). However, in one example, the spacer in the second zone 150 may be treated (e.g., by compression during molding) to a greater degree than spacer in the first zone 148. Thus, albeit the same spacer material(s) are present in the first and second zones 148 and 150, the second zone 150 exhibits less elasticity and is more rigid, as the spacer material(s) corresponding thereto is more compressed. Alternatively, the second zone 150 may be treated to a lesser degree than the spacer material in the first zone 148. In another alternative aspect, at least one of the first and second zones 148 and 150 include another material the other zone lacks (i.e., comprising a different knit or weave, or the like), such that the fabric and material composition of the first and second zones 148 and 150 is not the same. In one aspect, a first zone having a first material composition may include a first stretch characteristic, mold characteristic, and/or thickness, while a second zone having a second material composition different than the first composition may include a second stretch characteristic, mold characteristic, and/or thickness.

In one aspect, the thickness of the second layer 154 may vary. As illustrated in FIG. 11, a portion of the second layer 154 may be thicker than other portions of the second layer 154. These variances may be a result of one or more molding techniques. For example, the thickness between the surfaces indicated by arrows 156 and 158 may be greater than the thickness between the surfaces indicated between arrows 160 and 162. And in a further aspect, the thickness between the surfaces indicated between arrows 160 and 162 may be greater than the thickness between the surfaces indicated between arrows 164 and 166. In some aspects, the second layer 154 that corresponds to the second zone 150 of the left liner cup 132 may have a thickness that is less than the second layer 154 that corresponds to the first zone 148 of the left liner cup 132. It will be understood that thickness of the first and second layers 152 and 154 is merely one example of a physical difference resulting from a molding technique, which may be associated with one or more molding characteristics.

It will be understood that other methods of manufacture, molding techniques, and the like are considered to be within the scope of this disclosure such that the exemplary techniques discussed herein are not limiting. It will further be understood that the first and second zones 148 and 150 may differ in thickness, density, elasticity, and other characteristics such that these examples are not limiting.

Figure 12:
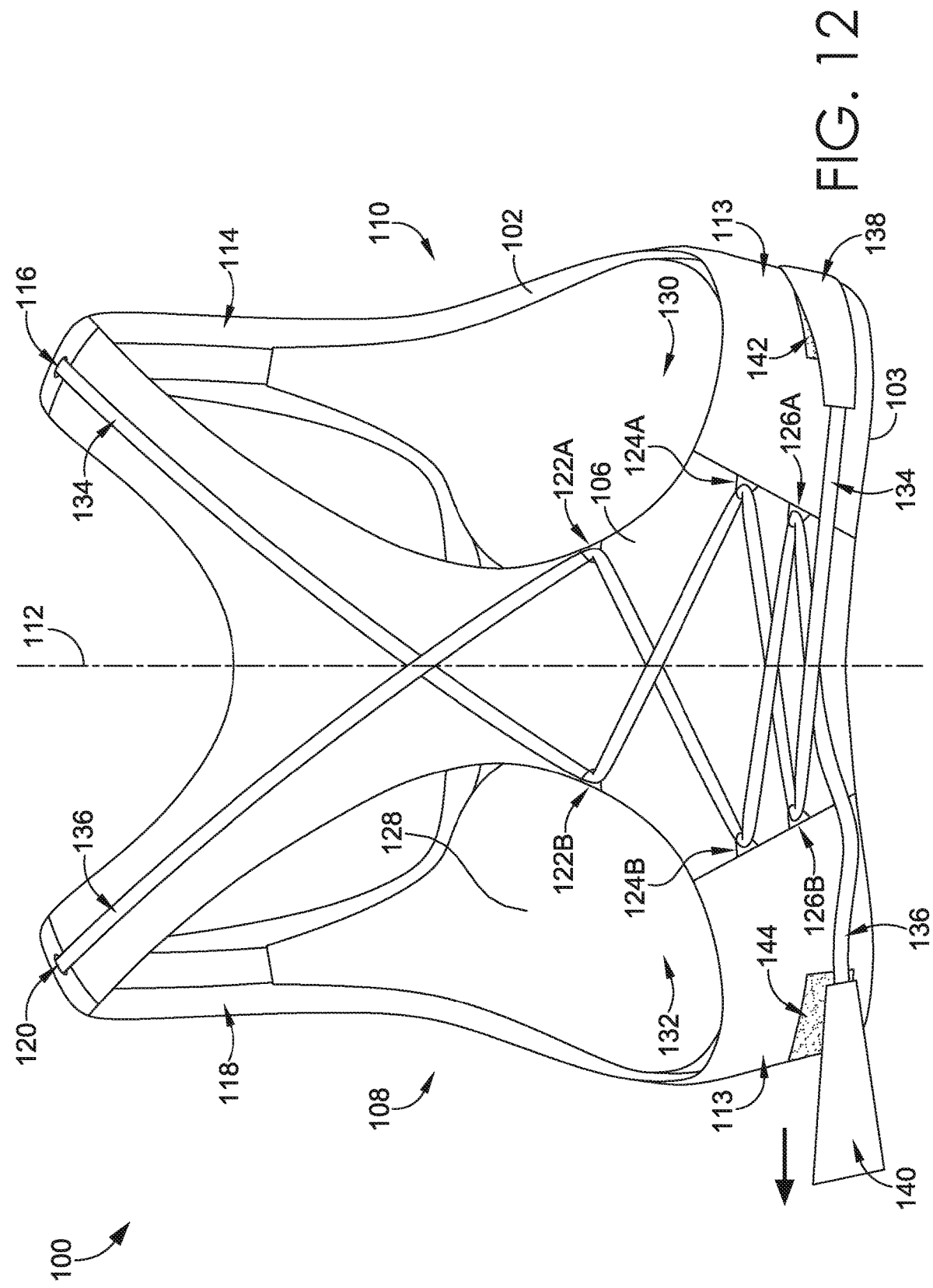
FIG. 12 depicts a rear view of the bra of FIG. 1 with a left harness strap in a detached position, in accordance with an aspect herein.
Figure 13:
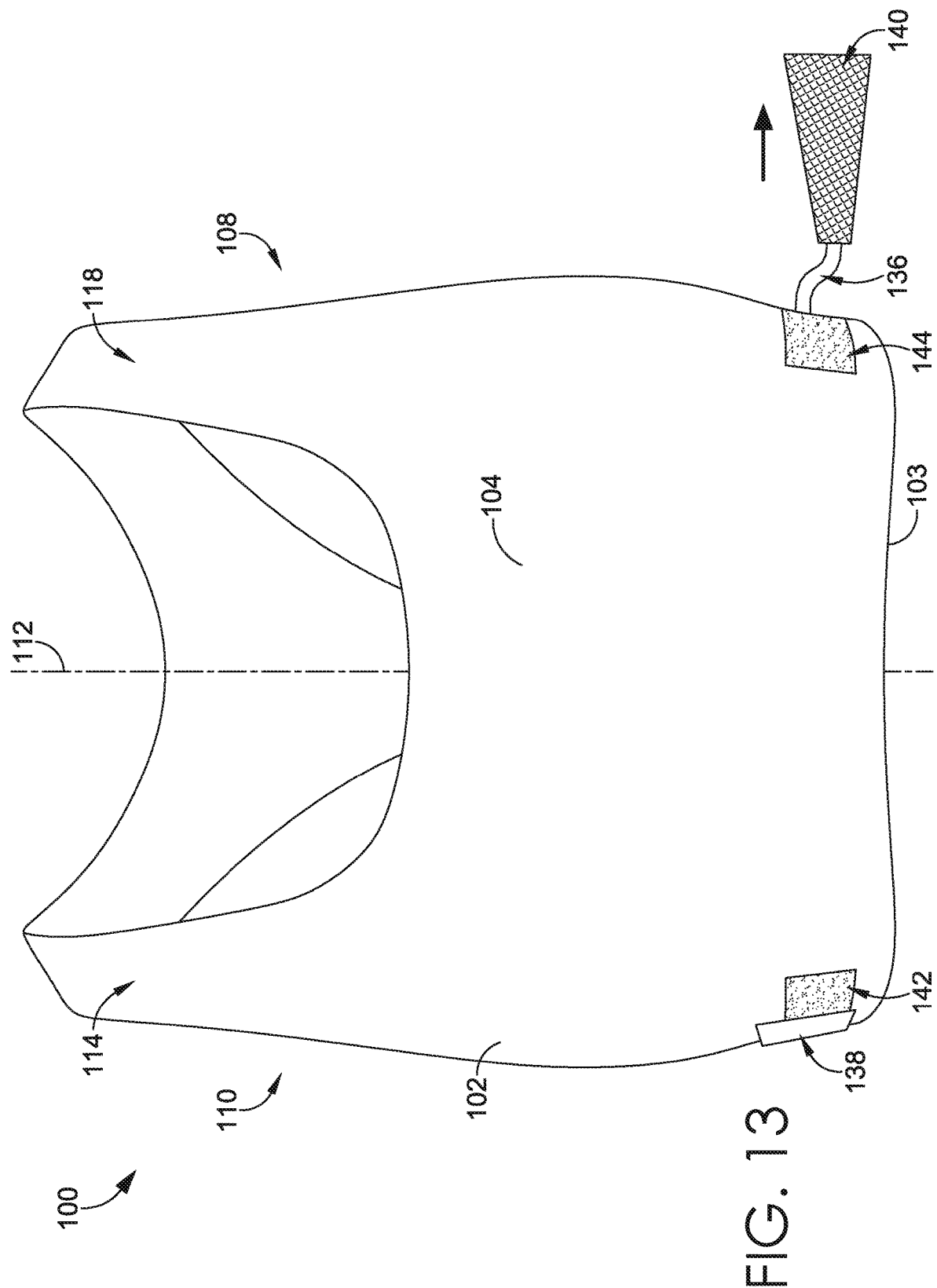
FIG. 13 depicts a front view of the bra of FIG. 1 with a left harness strap in a detached position, in accordance with an aspect herein.

As the interconnected features of the adjustable support harness system have been described, a description of an exemplary adjustment of the bra 100 is now provided. FIGS. 12-15 illustrate the exemplary movement of the left tab 140 in order to engage the harness system and adjust the bra 100. FIG. 12 depicts a rear view of the bra of FIG. 1 in accordance with an aspect herein and FIG. 13 depicts a front view of the bra of FIG. 1 in accordance with an aspect herein. In FIG. 12, the left tab 140, shown unattached to the left attachment element 144, is pulled away from the midline axis 112 and out from the left side 108 of the bra body 102. An arrow indicates the motion of pulling the left tab 140 away from the bra body 102. In FIG. 13, an arrow indicates the continued directional manipulation of the left tab 140 away from the midline axis 112 and away from the bra body 102.

Figure 14:
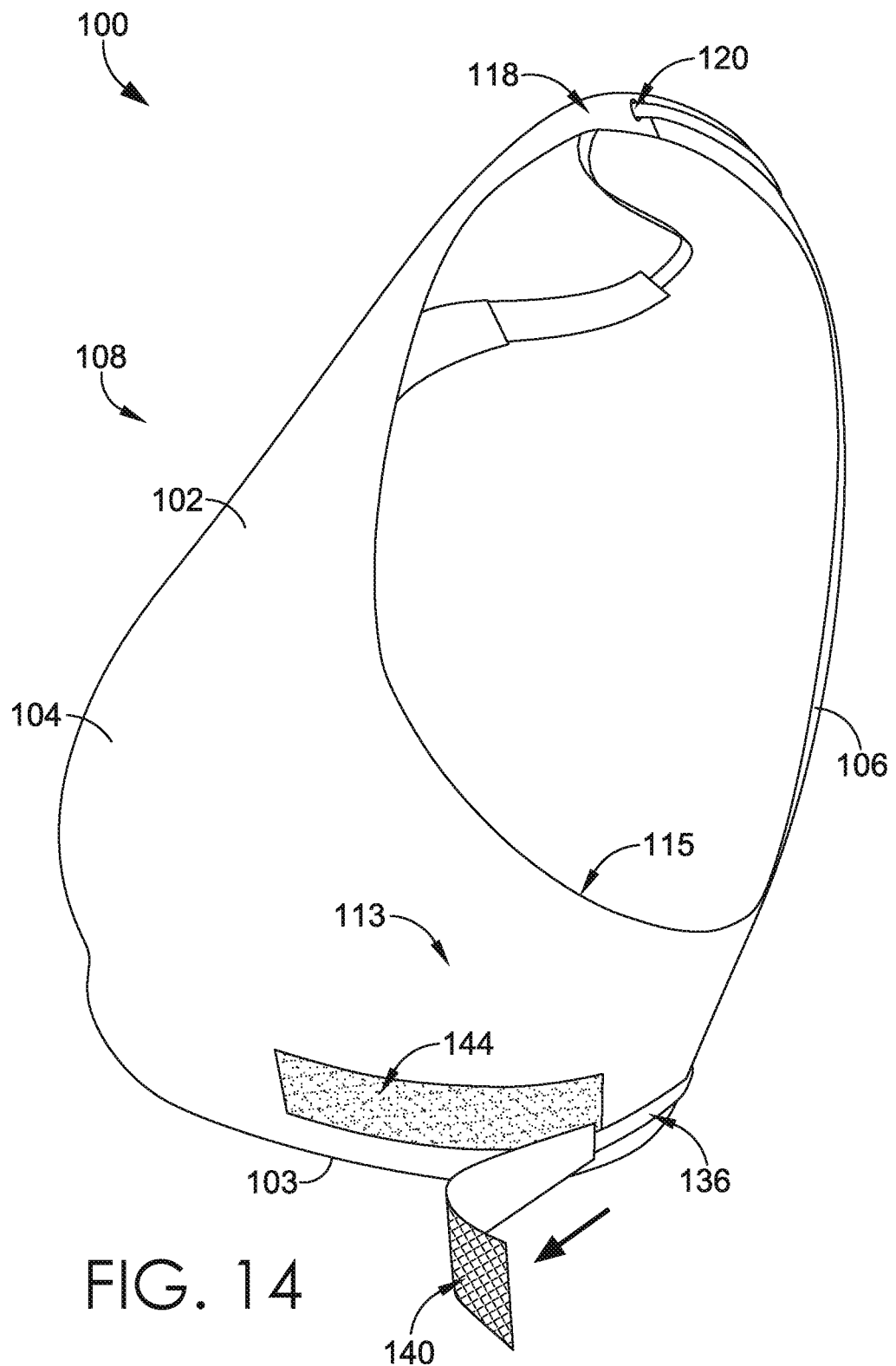
FIG. 14 depicts a side view of the bra of FIG. 1 with a left harness strap in a detached position, in accordance with an aspect herein.

FIG. 14 depicts a side view of the bra of FIG. 1, in accordance with an aspect herein. The movement and/or manipulation of the left tab 140 may be continued by pulling the left tab 140 toward the front portion 104 of the bra body 102. The left tab 140, being coupled to the left harness strap 136, exerts a force on an end of the left harness strap 136 coupled to the tab, thereby moving and pulling the left harness strap 136. When the left tab 140 is pulled forward, the left tab 140 and at least a portion of the left harness strap 136 begin to wrap around the left side 108 of the bra body 102. Additionally, the left harness strap 136 is pulled further through one or more of a series of maintainers at the back portion 106. In effect, the left harness strap 136 is being tightened (e.g., a physical length of a harness strap does not change, merely an effective length because, as more of a harness strap's length moves toward the front portion 104, less of the harness strap's length is available at the back portion 106).

Moreover, another portion of the left harness strap 136 slides from the interior to the exterior of the bra body 102 via the second aperture 120. The movement or sliding of the left harness strap 136 through the second aperture 120 creates an upward force on the left liner cup 132 to which the left harness strap 136 is attached. The left liner cup 132 is pulled upward toward the second aperture 120 as the left harness strap 136 escapes to the exterior of the bra body 102 via the second aperture 120. Therefore, as the left tab 140 is manipulated outward from the midline axis 112 and/or toward the front portion 104, the left liner cup 132 is lifted and/or shifted from a first support position to a second support position. The second support position may correspond to a change in support level, tightness, and/or degree of lift in comparison to the first support position or an initial position. When a desired support level, tightness, and/or degree of lift is met by a change in position of the right and/or left liner cups, the left tab 140 is coupled to the left attachment element 144 and/or the right tab 138 is coupled to the right attachment element 142.

Figure 15:
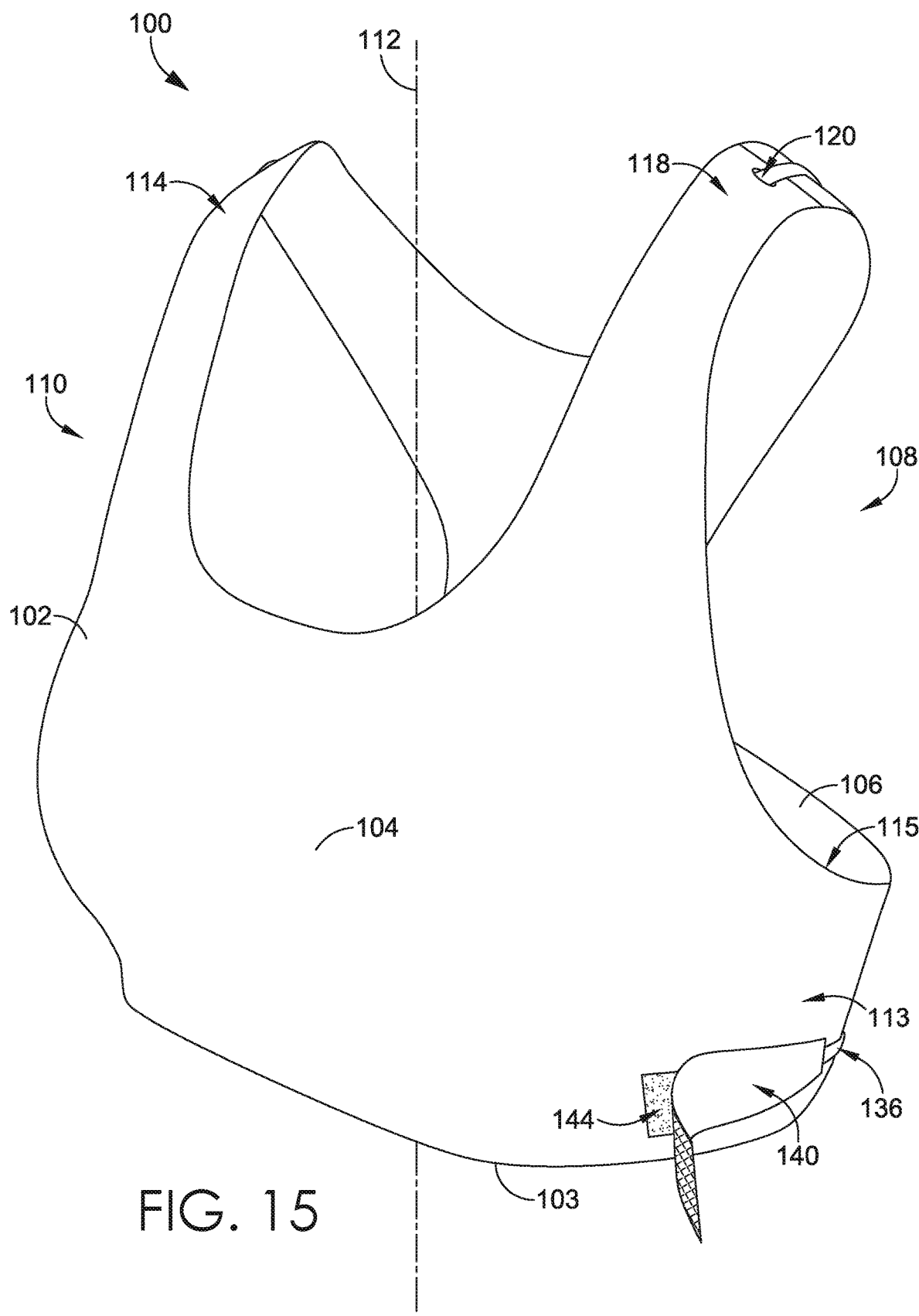
FIG. 15 depicts a front, perspective view of the bra of FIG. 1 with a left harness strap in a partially attached position, in accordance with an aspect herein.

And at FIG. 15, it depicts a perspective view of the bra of FIG. 1 in accordance with an aspect herein. The left tab 140 is depicted as partially coupled (e.g., in the process of being coupled) to the left attachment element 144. In one aspect, when the left tab 140 is coupled to the left attachment element 144, a fastener or fastening mechanism holds the left tab 140 in place, securing the harness system at the desired support level, tightness, and/or degree of lift. Exemplary fasteners include hook-and-loop type fasteners, ties, buttons, snaps, and the like. Similarly, when the bra 100 is in an as-worn configuration, manipulating the right tab 138 away from the midline axis 112 and toward the front portion 104 adjusts a length of the right harness strap 134 and shifts the right liner cup 130 from a first support position to a second support position.

In this way, manipulating the right and left harness straps 134 and 136 may be used to customize the fit of the bra 100 and/or to customize a support level for an activity. By manipulating one or more of the right and left tabs 138 and 140 and coupling each to one of the right and left attachment elements 142 and 144, each of the right and left harness straps 134 and 136 may be effectively tightened or loosened and each of the liner cups may be adjusted. Tightening of the right and left harness straps 134 and 136 creates an upward force (e.g., a pull) on each respective right and left liner cups 130 and 132. The upward force moves or shifts one or more of the right and left liner cups 130 and 132 upward (e.g., a lift) with respect to the midline axis 112, from a first support position to a second support position. Generally, the second support position may provide more support and stability to the breast tissue than the first support position, such that breast tissue is secured and breast tissue movement is reduced or minimized. The second support position may be achieved by placing the tab as close as possible to the front portion 104. Compared to the second support position, the first support position of a liner cup may provide less support and reduced stability to the breast tissue so that breast tissue may have a greater degree of movement in the cup liner 128. The first support position may be achieved by placing the tab close to the back portion 106. As will be understood in the art, a wearer may desire greater or less support depending on a physical activity. Therefore, tightening a harness strap via the harness system enables the bra 100 to provide increased support. The closer a tab is placed to the front portion 104, the greater the degree of breast tissue support, cup lift, and back posture support may be provided by the bra 100.

The adjustment provided by the harness system described herein provides that one single manipulation, applied separately to each side of a bra 100, may be used to adjust a length of a harness strap, a degree of lift of a liner cup, and an amount of back or posture support.

Figure 16:
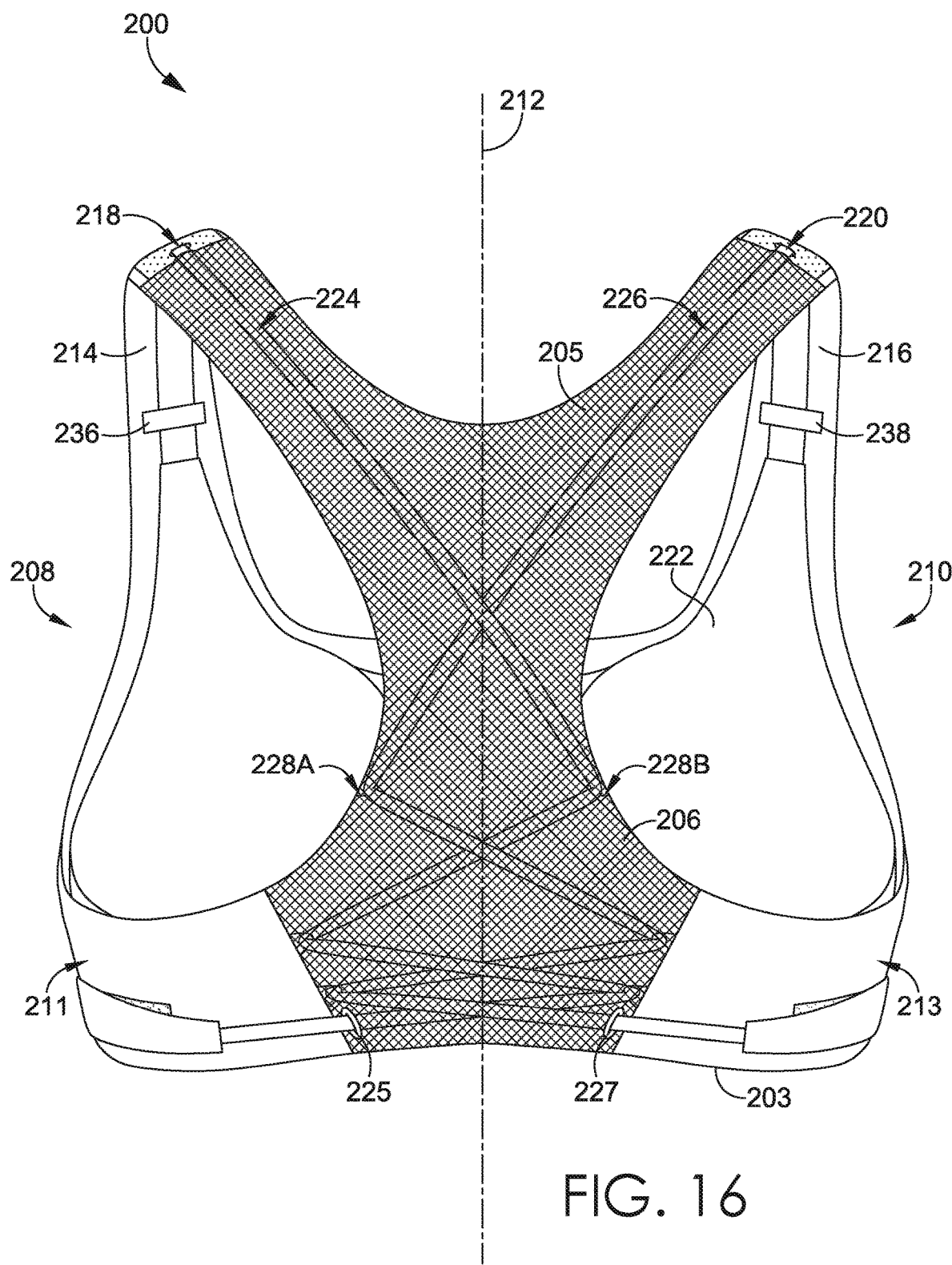
FIG. 16 depicts a rear view of a bra having adjustable support provided by a harness system, in accordance with an aspect herein.
Figure 17:
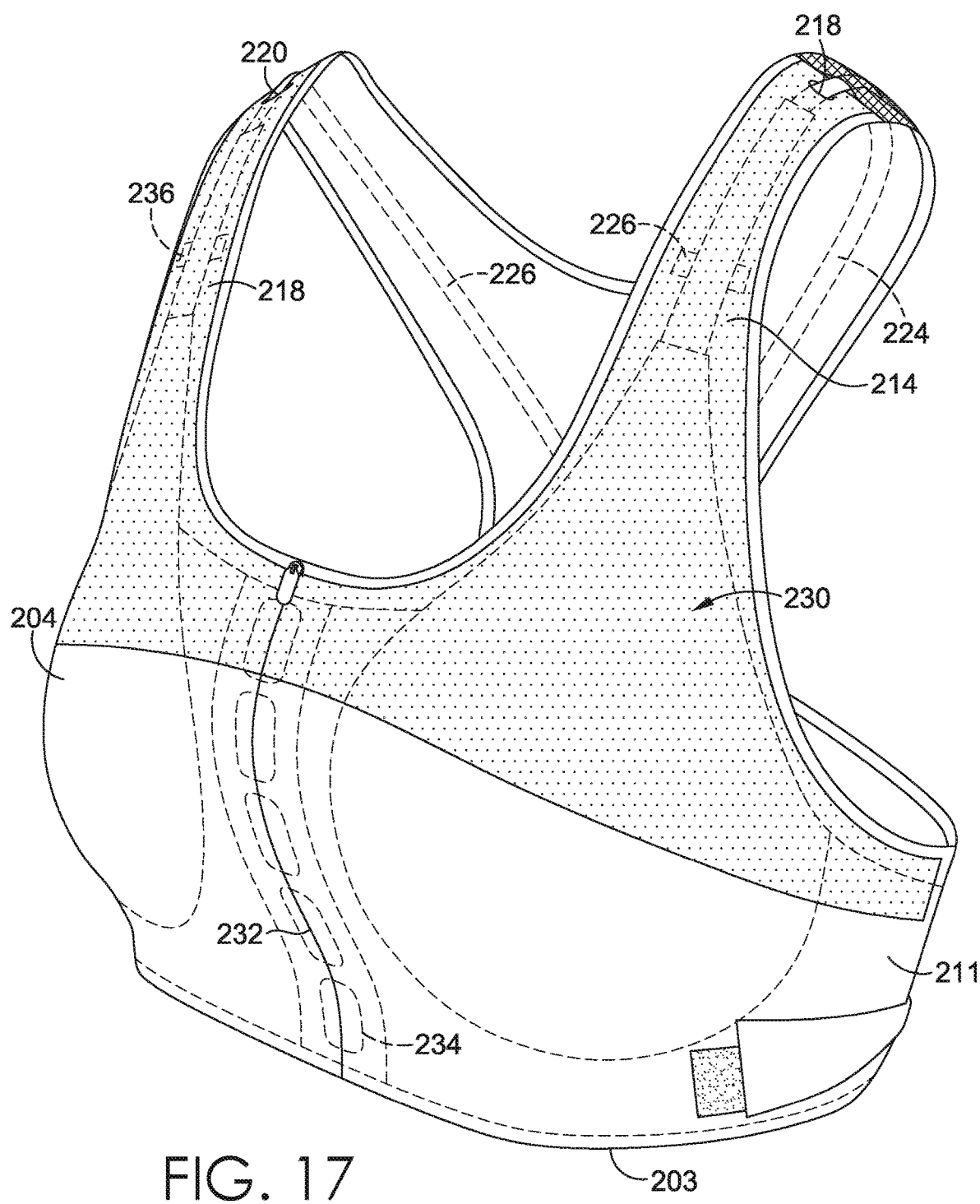
FIG. 17 depicts a front, perspective view of the bra of FIG. 16, in accordance with an aspect herein.

FIGS. 16 and 17 depict an exemplary garment 200 including an adjustable harness system in accordance with an aspect herein. In one aspect, the exemplary garment 200 includes a front portion 204, a back portion 206, a lower margin 203, a first side 208 and a second side 210 determined with respect to a hypothetical midline axis 212, a first underarm area 211, a second underarm area 213, a first shoulder strap 214, and a second shoulder strap 216, similar to those previously described with respect to illustrative FIG. 1. The first shoulder strap 214 and the second shoulder strap 216 have a first opening 218 and second opening 220, respectively, in one aspect. The garment 200 further comprises a liner 222, a first harness strap 224, and a second harness strap 226, similar to those previously described with respect to illustrative FIG. 1, in some aspects. And in some aspects, the back portion 206 further includes one or more pairs of maintainers, including a first maintainer 228A and a second maintainer 228B, as determined with respect to the hypothetical midline axis 212, wherein the first maintainer 228A corresponds to the first side 208 and the second maintainer 228B corresponds to the second side 210, in one aspect. Generally, the position of the first harness strap 224 and the second harness strap 226 within the apex region of the first shoulder strap 214 or the second shoulder strap 216, respectively, is maintained by the first opening 218 and the second opening 220, as have been previously described.

Other elements shown in FIGS. 16 and 17 may be similar to those previously discussed in detail herein.

The first harness strap 224 and the second harness strap 226 are laced through maintainers of the back portion 206 or are otherwise tethered to attachment points of the back portion 206, in aspects. In the aspect of FIGS. 16 and 17, at least a portion of the back portion 206 is overlaid with a layer of fabric such as, for example, a mesh fabric. In one such aspect, the overlay portion 205 is a layer of fabric that covers a portion of the back portion 206 corresponding to the first harness strap 224 and the second harness strap 226 as they are laced through maintainers. Accordingly, the overlay portion 205 may reduce opportunities for the first harness strap 224, the second harness strap 226, and maintainers to be caught, snagged, or pulled accidentally, for example. In some aspects, the overlay portion 205 provides for increased protection of the adjustable harness system while providing at least some visibility allowing for inspection of the adjustable harness system. Exemplary fabrics might include a sheer fabric, a mesh fabric, lace, burn-out fabric, fabric treated to have perforations or cut-outs, or a knit fabric. In aspects having an overlay portion 205, a third opening 225 and a fourth opening 227 may be present in the overlay portion 205 to enable the first harness strap 224 and the second harness strap 226 to pass through the overlay portion 205 so that the first harness strap 224 and the second harness strap 226 are exteriorly accessible.

Additionally, one or more portions of the garment 200 may be coated or treated in order to increase the modulus of elasticity of those one or more portions, in some aspects. In the aspect of FIGS. 16 and 17, an upper portion 230 of the front portion 204 is treated to increase the modulus of elasticity and further, in some aspects, to create lockdown, as previously described herein. By increasing the modulus of elasticity of the upper portion 230, for example, upward and/or outward movement of breast tissue may be reduced, or further, minimized. Similarly, a portion surrounding each of the first opening 218 and the second opening 220 may be treated to increase the modulus of elasticity, in one aspect. Exemplary treatments include coating the material, either at the surface of the material or by coating fibers, with a material such as polyurethane (PU). By increasing the modulus of elasticity at, near, or surrounding each of the first opening 218 and the second opening 220, the first opening 218 and the second opening 220 are reinforced by the added rigidity, for example. Additionally, the increased modulus of elasticity may prevent fraying or tearing of materials at or near the first opening 218 and the second opening 220, in some aspects.

Continuing with FIGS. 16 and 17, in some aspects, the garment 200 includes releasable closures for donning and doffing the garment 200. In the aspect of FIGS. 16 and 17, the body 202 includes a closure 232 for repeatedly opening and closing the body 202 at the front portion 204. Additionally or alternatively, the liner 222 comprises one or more fasteners 234 for opening and closing the liner 222 toward the front portion 204, in some aspects. In one aspect, the body 202 and the liner 222 are attached to one another in a lengthwise manner (e.g., with stitching, heat bonding, or adhesives) along the front portion 204 that corresponds to the closure 232 and the one or more fasteners 234. Accordingly, the body 202 and the liner 222 may be donned and doffed together as attached to one another, in such aspects. Exemplary closures and fasteners include zippers, snaps, buttons, hook-and-eye mechanisms, and hook-and-loop type fasteners, for example.

In one aspect, the body 202 is permanently affixed to the liner 222 lengthwise (as previously described with respect to a lower margin 203 and a hypothetical midline axis 212) along the closure 232 and the one or more fasteners 234. In another aspect, the body 202 is not permanently affixed, but is "releaseably" affixed to the liner 222 such that the liner 222 can be attached, detached, and reattached to the body 202 when desired. Additionally or alternatively, the body 202 and liner 222 may be continuously affixed to one another, or non-continuously affixed to one another using one or more attachment points, for example. The body 202 and liner 222 may be attached to one another using stitching, adhesives, snaps, and buttons, for example. However, the aspect depicted in FIGS. 16 and 17 should not be construed as limiting and aspects lacking such closures and/or fasteners are considered to be within the scope of this disclosure.

And, in some aspects, a first harness strap 224 and the second harness strap 226 are each tethered, loosely, to the first shoulder strap 214 and the second shoulder strap 216. The tethering is accomplished using a maintainer or a strip to create an opening through which a harness strap is passed, is one such aspect. As shown in exemplary FIG. 16, the first harness strap 224 is loosely held by a first positioning strip 236 and the second harness strap 226 is held a second positioning strip 238. The first harness strap 224 is held between the first shoulder strap 214 and the first positioning strip 236, as the first positioning strip 236 is attached to the first shoulder strap 214, in one such aspect. And the second harness strap 226 is held between the second shoulder strap 216 and the second positioning strip 238, for example. Generally, the first positioning strip 236 and the second positioning strip 238 are attached to respective shoulder straps in order to confine respective harness straps therein. This may reduce lateral or side-to-side slippage of the harness straps during adjustment, for example.

The disclosure provided above is intended to illustrate some possible combinations of various aspects associated with the adjustable support bra with harness system. Those skilled in the art will understand, however, that within each embodiment, some features may be optional. Moreover, different features discussed in different embodiments could be combined in still other embodiments and would still fall within the scope of the attached claims. Some features could be used independently in some embodiments, while still other features could be combined in various different ways in still other embodiments. The purpose served by the disclosure, however, is to provide an example of the various features and concepts related to the aspects described herein, not to limit the scope thereof. One skilled in the relevant art will recognize that numerous variations and modifications may be made to the configurations described above without departing from the scope of aspects described herein, as defined by the claims.

What is claimed is:

1. An article of apparel comprising:
a body having a front portion, a back portion, a first side portion, a second side portion, a first shoulder strap extending between the front portion and the back portion and including a first aperture, and a second shoulder strap extending between the front portion and the back portion and including a second aperture;
a liner positioned internal to at least the front portion, the first side portion, and the second side portion of the body, the liner having a first harness strap adapted to extend through the first aperture and terminating in a first tab, the liner further having a second harness strap adapted to extend through the second aperture and terminating in a second tab;
a first attachment element located on the first side portion of the body; and
a second attachment element located on the second side portion of the body, wherein the first tab is adapted to be adjustably secured to one of the first attachment element or the second attachment element, and wherein the second tab is adapted to be adjustably secured to one of the first attachment element or the second attachment element.

2. The article of apparel of claim 1, wherein the liner comprises at least a first side at least partially aligned with the first side portion of the body, and a second side at least partially aligned with the second side portion of the body, wherein the first harness strap of the liner is located on the first side of the liner, and wherein the second harness strap of the liner is located on the second side of the liner.

3. The article of apparel of claim 1, wherein when the first tab is secured to one of the first attachment element or the second attachment element, the liner is adjusted from a first support position to a second support position.

4. The article of apparel of claim 1, wherein when the second tab is secured to one of the first attachment element or the second attachment element, the liner is adjusted from a first support position to a second support position.

5. The article of apparel of claim 1, wherein the liner further comprises a first liner cup, and wherein when the first tab is secured to one of the first attachment element or the second attachment element, the first liner cup is adjusted from a first support position to a second support position.

6. The article of apparel of claim 5, wherein the liner further comprises a second liner cup, and wherein when the second tab is secured to one of the first attachment element or the second attachment element, the second liner cup is adjusted from a third support position to a fourth support position.

7. The article of apparel of claim 1, wherein the back portion comprises a first pair of maintainers, and wherein the first harness strap is further adapted to pass through at least a first maintainer of the first pair of maintainers.

8. The article of apparel of claim 1, wherein the back portion comprises a first pair of maintainers, and wherein the second harness strap is further adapted to pass through at least a first maintainer of the first pair of maintainers.

9. An article of apparel comprising:
a body comprising a front portion, a back portion, a first side, a second side, a first shoulder strap having a first aperture, and a second shoulder strap having a second aperture, the back portion comprising a first pair of maintainers;
a first attachment element located on the first side of the body;
a second attachment element located on the second side of the body; and
a liner positioned internal to the body, the liner having a first harness strap and a second harness strap, wherein the first harness strap is adapted to pass through the first aperture and at least a first maintainer of the first pair of maintainers, the first harness strap having a first tab adapted to attach to the first attachment element, and wherein the second harness strap is adapted to pass through the second aperture and at least a second maintainer of the first pair of maintainers, the second harness strap having a second tab that is adapted to attach to the second attachment element.

10. The article of apparel of claim 9, wherein the liner comprises at least a first side at least partially aligned with the first side of the body, and a second side at least partially aligned with the second side of the body, wherein the first harness strap of the liner is located on the first side of the liner, and wherein the second harness strap of the liner is located on the second side of the liner.

11. The article of apparel of claim 9, wherein when the first tab of the first harness strap is attached to the first attachment element, the liner is adjusted from a first support position to a second support position.

12. The article of apparel of claim 9, wherein the liner further comprises a first liner cup, and wherein when the first tab of the first harness strap is attached to the first attachment element, the first liner cup is adjusted from a first support position to a second support position.

13. The article of apparel of claim 9, wherein when the second tab of the second harness strap is attached to the second attachment element, the liner is adjusted from a first support position to a second support position.

14. The article of apparel of claim 9, wherein the liner further comprises a second liner cup, and wherein when the second tab of the second harness strap is attached to the second attachment element, the second liner cup is adjusted from a first support position to a second support position.

15. The article of apparel of claim 9, wherein the first shoulder strap is located on the first side of the body and wherein the second shoulder strap is located on the second side of the body.

16. The article of apparel of claim 9, wherein each of the first pair of maintainers is positioned on different sides of a midline axis, and wherein the first harness strap crosses the midline axis an even number of times.

17. The article of apparel of claim 9, wherein each of the first pair of maintainers is positioned on different side of a midline axis, and wherein the second harness strap crosses the midline axis an even number of times.

18. The article of apparel of claim 9, wherein the first pair of maintainers comprises two maintainers.

19. The article of apparel of claim 9, wherein the first pair of maintainers comprises three or more maintainers.

20. An article of apparel comprising:
a body comprising a front portion, a back portion comprising a first pair of maintainers, a first side having a first shoulder strap with a first aperture, and a second side having a second shoulder strap with a second aperture;
a first attachment element located on the first side of the body;
a second attachment element located on the second side of the body; and
a liner positioned internal to the body, the liner comprising a first side and a second side, the liner having a first harness strap on the first side of the liner and a second harness strap on the second side of the liner, wherein the first harness strap is adapted to pass through the first aperture and at least a first maintainer of the first pair of maintainers, the first harness strap having a first tab that is adapted to attach to the first attachment element, and wherein the second harness strap is adapted to pass through the second aperture and at least a second maintainer of the first pair of maintainers, the second harness strap having a second tab that is adapted to attach to the second attachment element.

* * * * *

UNITED STATES PATENT AND TRADEMARK OFFICE
CERTIFICATE OF CORRECTION

PATENT NO. : 11,185,114 B2
APPLICATION NO. : 16/454312
DATED : November 30, 2021
INVENTOR(S) : Stephanie Muhlenfeld Page 1 of 1

It is certified that error appears in the above-identified patent and that said Letters Patent is hereby corrected as shown below:

In the Specification

Column 1, Line 8:
"ment with Harness System", is a application of U.S. Pat. No."
Should read:
-- ment with Harness System", is a continuation application of U.S. Pat. No. --.

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*